（12) United States Patent
Martin et al.

(10) Patent No.: US 8,420,805 B2
(45) Date of Patent: Apr. 16, 2013

(54) PROCESS FOR PREPARING PROPHYRIN DERIVATIVES, SUCH AS PROTOPROPHYRIN (IX) AND SYNTHESIS INTERMEDIATES

(75) Inventors: Pierre Martin, Rheinfelden (CH); Markus Mueller, Wegenstetten (CH); Dirk Spielvogel, Lorach (DE); Dietmar Flubacher, Bad Krozingen (DE); Andreas Boudier, Basel (CH)

(73) Assignee: Sanofi Pasteur S.A., Lyon (FR)

( * ) Notice: Subject to any disclaimer, the term of this patent is extended or adjusted under 35 U.S.C. 154(b) by 0 days.

(21) Appl. No.: 13/218,149

(22) Filed: Aug. 25, 2011

(65) Prior Publication Data

US 2011/0306761 A1 Dec. 15, 2011

Related U.S. Application Data

(62) Division of application No. 12/057,574, filed on Mar. 28, 2008, now Pat. No. 8,026, 358.

(60) Provisional application No. 60/943,735, filed on Jun. 13, 2007.

(30) Foreign Application Priority Data

Mar. 30, 2007 (FR) ...................... 07 02334

(51) Int. Cl.
*C07D 487/22* (2006.01)
(52) U.S. Cl.
USPC ........................................ 540/145
(58) Field of Classification Search ............ 540/145
See application file for complete search history.

(56) References Cited

PUBLICATIONS

Jackson, et al., "Synthetic and Biosynthetic Studies of Porphyrins. Part 11. [1] The Synthesis of meso Oxygenated Protoporphyrins[2]," J. Chem. Soc. Perkin Trans I pp. 307-312 (1987).
Smith, et al., "Syntheses of Derivatives of Protoporphyrin IX Bearing Deuteriated Methyls on the Propionate (C and D) Rings," J. Org. Chem., vol. 51, No. 24 pp. 4660-4667 (1986).
Jackson, et al., "Reactions on Solid Supports Part II: A Convenient Method for Synthesis of Pyrromethanes Using a Montmorillonite Clay as Catalyst," Tetrahedron Letters vol. 26, No. 6 pp. 793-796 (1985).
Al-Hazimi, et al., "Synthetic and Biosynthetic Studies of Porphyrins. Part 7. [1,2] The Action of Coproporphyrinogen Oxidase on Coproporphyrinogen-IV: Syntheses of Protoporphyrin-XIII, Mesoporphyrin XIII, and related Tricarboxylic Porphyrins," J. Chem. Soc. Perkin Trans. 1 pp. 265-276 (1987).
Chong, et al., "VII.* Synthesis of 5,5'-Diformyldipyrrylmethanes," Aust. J. Chem., 22 pp. 229-238 (1969).
Cavaleiro, et al., "Pyrroles and Related Compunds. Part XXXIII.[1] Total Synthesis of Deuteriated Derivatives of Protoporphyrin-IX for Nuclear Magnetic Resonance Studies of Haemoproteins [2]," J. Chem. Soc. Perkin I pp. 1771-1781 (1974).
Cavaleiro, et al., "Pyrroles and Related Compunds. Part XXII.[1] Syntheses of Pyrromethanes and a Tripyrrane [2]," J. Chem. Soc. Perkin I pp. 2471-2478 (1973).

Rezzano, Irene, et al., "Carbon-5 Regiospecific Synthesis of Deuteroporphyrin IX," J. Org. Chem., 1982, vol. 47, pp. 3059-3063.
Cavaleiro, Jose, A.S., et al., "Pyrroles and Related Compounds, Part XXXII, Biosynthesis of Protoporphyrin-IX from Coproporphyrinogen-III," J.C.S. Perkin I, 1974, pp. 1188-1194.
Nakae, Yoshinori, et al., "The Convenient Screening Method using Albumin for the Tumor Localizing Property of Ga-Porphyrin Complexes," Journal of Photochemistry and Photobiology A: Chemistry, 2005, vol. 172, pp. 55-61.

*Primary Examiner* — Brian McDowell
(74) *Attorney, Agent, or Firm* — McDonnell Boehnen Hulbert & Berghoff LLP

(57) ABSTRACT

The present invention relates to a process for preparing a porphyrin of formula (I), optionally in the form of a salt with an alkali metal and/or in the form of a metal complex:

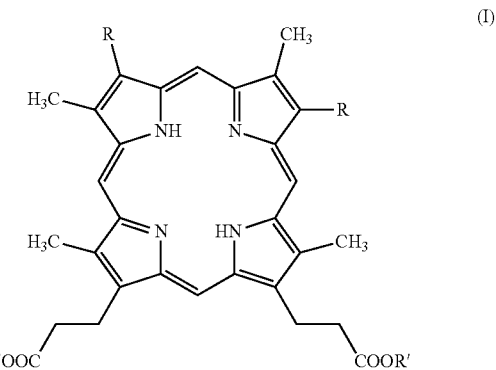

in which:
R and R' are as defined in claim 1,
comprising:
a step of condensation, in an acidic medium, between a dipyrromethane of formula (II):

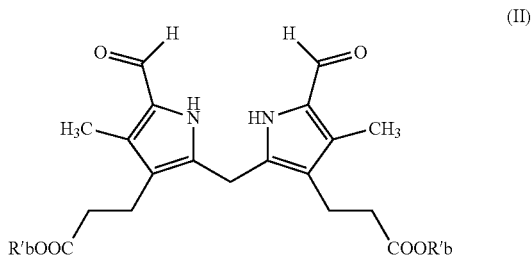

in which R'b is as defined above for (I),
and a dipyrromethane of formula (III):

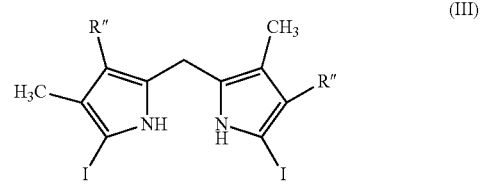

in which R" is as defined in claim 1, and also the compounds of formula (III).

14 Claims, No Drawings

PROCESS FOR PREPARING PROPHYRIN DERIVATIVES, SUCH AS PROTOPROPHYRIN (IX) AND SYNTHESIS INTERMEDIATES

CROSS-REFERENCE TO RELATED APPLICATIONS

This application is a divisional application of U.S. patent application Ser. No. 12/057,574, filed Mar. 28, 2008, which claims priority to and incorporates by reference U.S. provisional patent application No. 60/943,735 filed Jun. 13, 2007 and French patent application number FR 07 02334 filed Mar. 30, 2007.

BACKGROUND OF THE INVENTION

1. Field of the Invention

The present invention relates to a novel process for preparing porphyrin derivatives, such as protoporphyrin (IX), and also to intermediates for the synthesis of these compounds.

2. Summary of the Related Art

Certain porphyrins are known and used for their biological or medical properties. By way of example, mention may be made of the following porphyrins of formula:

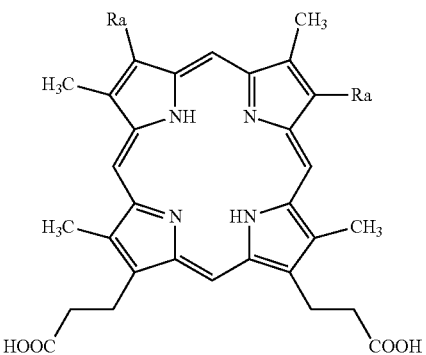

in which:
Ra=—CH=CH$_2$, then named protoporphyrin IX,
Ra=—CH$_2$CH$_3$, then named mesoporphyrin,
Ra=—CH(OH)CH$_3$, then named hematoporphyrin,
Ra=H, then named deuteroporphyrin,
Ra=—CH$_2$CH$_2$COORb with Rb being a hydrogen atom or a methyl, ethyl, n-propyl or i-propyl group, then named coproporphyrin III,
Ra=—C(O)CH$_3$, then named diacetyldeuteroporphyrin.

These porphyrins can be used in the form of salts, for example of a salt with an alkali metal at the two acid functions, such as a sodium salt.

It is also possible, depending on the applications, for these porphyrins to be used in a complexed form, for example complexed with a metal such as Fe, or alternatively a metal salt such as FeCl or FeOH. The complex of protoporphyrin IX with Fe is called heme, that with FeOH is called hematin and that with FeCl is called hemin.

These porphyrins are most commonly prepared by hemisynthesis, which poses the problem of impurities of animal origin, in particular, that may be present. For certain applications, for example in the case of protoporphyrin (IX), or of its sodium salt, which may be used in cell culture media, the desire is to provide a completely synthetic preparation process which uses only products of synthetic origin. Certain processes of preparation by chemical synthesis of these compounds have already been proposed. The publications in JCS Perkin I, 1974, 1771-1781 and 1188-1194, for example, describe the preparation of protoporphyrin IX. A known method for preparing protoporphyrin, to which reference is made in these publications, is referred to as the MacDonald process and consists in coupling, in the presence of a metal cation $M^+$ such as $Zn^{2+}$ or $Fe^{3+}$, the following two pyrromethanes (A) and (B):

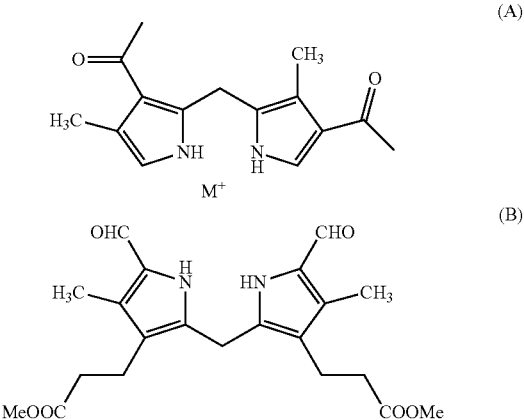

so as to give a porphodimethane structure (C):

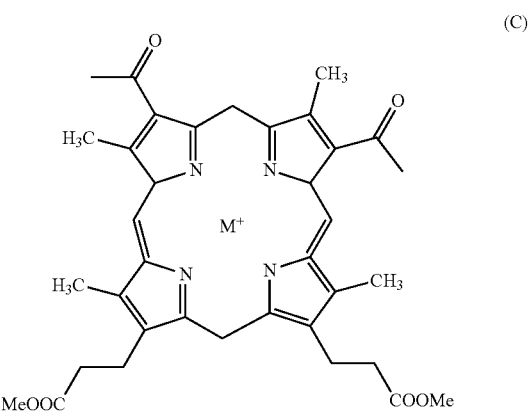

which must subsequently be oxidized so as to form the metalated porphyrin (D):

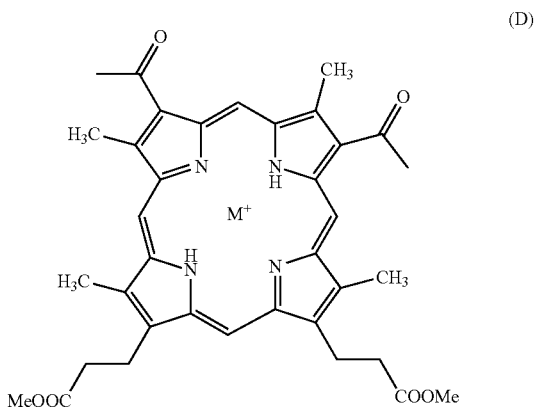

Such a method is in particular described in Science of Synthesis Houben-Weyl, vol. 17, 1081-1235 and in The porphyrin Handbook, vol. 1, synthesis and Chemistry, Academic Press, Boston, 2000.

It is subsequently necessary to demetalize the porphyrin, in the presence of sulfuric acid, if said porphyrin must be used in free form. The latter step in particular is not quantitative and the porphyrin obtained does not have a satisfactory degree of purity. The high —C(O)CH$_3$ function must also be converted to —CH=CH$_2$.

SUMMARY OF THE INVENTION

In this context, the present invention proposes to provide a new synthetic preparation process free of any contaminant of animal origin, which makes use of only products of synthetic origin, and which is suitable, in particular, for the synthesis of protoporphyrin IX, of mesoporphyrin, of hematoporphyrin, of deuteroporphyrin, of coproporphyrins III and of diacetyl-deuteroporphyrin, optionally in the form of salts. This process must in particular allow them to be produced with high yields and a high degree of purity. The process according to the invention must also be readily industrializable and show good profitability. The process developed in the context of the invention makes it possible, in addition, to prevent the intermediate formation of a metalated porphyrin.

DETAILED DESCRIPTION OF THE PREFERRED EMBODIMENTS

In this context, the invention relates to a process for preparing a porphyrin of formula (I), optionally in the form of a salt:

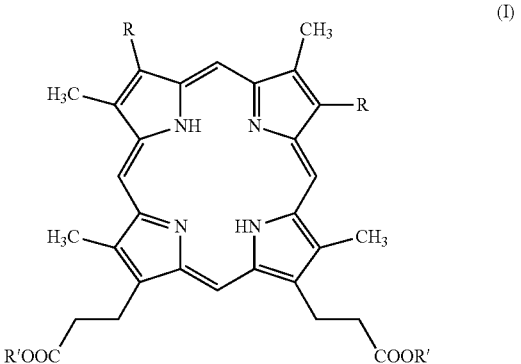
(I)

in which:
R is a hydrogen atom or a group selected from: —CH=CH$_2$, —CH$_2$—CH$_3$, —CH(OH)CH$_3$, —C(O)CH$_3$ and —CH$_2$CH$_2$COOR'a, with R' being a hydrogen atom or a methyl, ethyl, n-propyl or i-propyl group,
R' is a hydrogen atom or a group R'b selected from methyl, ethyl, n-propyl or i-propyl,
comprising:
a step of condensation, in an acidic medium, between a dipyrromethane of formula (II):

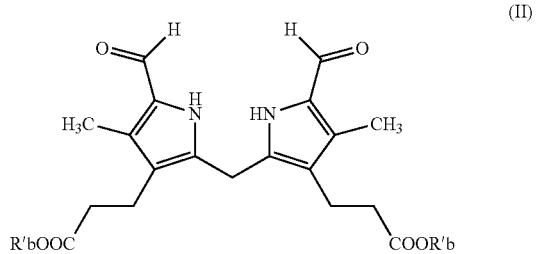
(II)

in which R'b is as defined above for (I), and a dipyrromethane of formula (III):

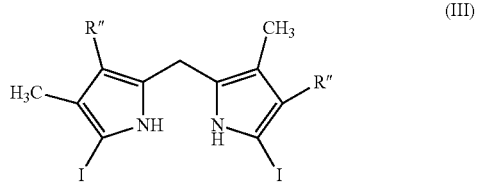
(III)

in which R" is selected from hydrogen, —CH=CH$_2$, —CH$_2$—CH$_3$, —CH(OH)CH$_3$, —C(O)CH$_3$, —CH$_2$CH$_2$OH, —CH$_2$CH$_2$OC(O)CH$_3$ and —CH$_2$CH$_2$Cl or —CH$_2$CH$_2$COOR'a, wherein R'a is hydrogen, methyl, ethyl, n-propyl, or i-propyl, and R" is either identical to R as defined above for (I) or is a precursor of R, so as to form the porphyrin of formula (I'):

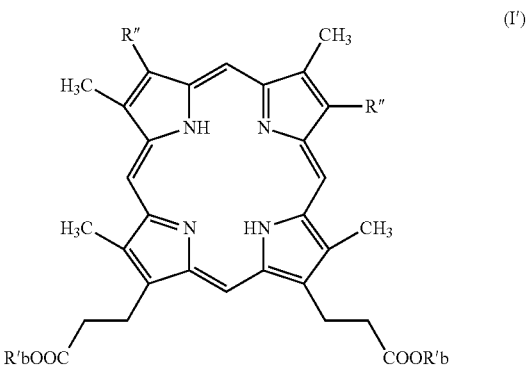
(I')

in which R" and R'b are as defined above for (II) and (III), and:
when R" is a precursor of R, further comprising converting R" to R, and
when R'=H, further comprising eliminating R'b so as to form —COOH moieties, optionally in the form of a salt.

The process according to the invention makes it possible to obtain porphyrins that have a satisfactory solubility, in particular in an aqueous solution. A subject of the present invention is also the porphyrins of formula (I):

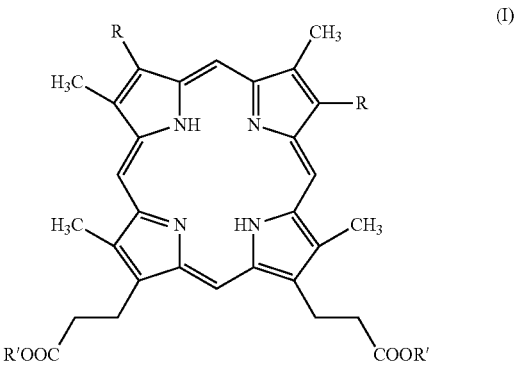
(I)

in which:
R is a hydrogen atom or a group selected from: —CH=CH₂, —CH₂—CH₃, —CH(OH)CH₃, —C(O)CH₃ and —CH₂CH₂COOR'a, with R' a being a hydrogen atom or a methyl, ethyl, n-propyl or i-propyl group,
R' is a hydrogen atom or a group R'b selected from methyl, ethyl, n-propyl or i-propyl,
and also the salts thereof that can be obtained according to the process of the invention.

By way of example of salts with porphyrins of formula (I), mention may, for example, be made of salts with an organic or inorganic base. In particular such salts may be formed with the porphyrins of formula (I) which comprise a carboxylic acid function; it is preferably an alkali metal salt, in particular a sodium, potassium or lithium salt, or an ammonium salt, an organic amine salt or a salt of an amino acid such as arginine or lysine.

It is also possible to form salts of the porphyrins of formula (I) with an inorganic or organic acid, which enable, for example, a suitable separation or crystallization of the compounds of formula (I), and also pharmaceutically acceptable salts. As appropriate acid, mention may be made of: picric acid, oxalic acid or an optically active acid, for example a tartaric acid, a dibenzoyltartaric acid, a mandelic acid or a camphosulfonic acid, and those which form physiologically acceptable salts, such as the hydrochloride, hydrobromide, sulfate, hydrogen sulfate, dihydrogen phosphate, maleate, fumarate, 2-naphthalenesulfonate or para-toluenesulfonate.

The salts of the compounds of formula (I) are prepared according to techniques well known to those skilled in the art, by incorporating the corresponding step of formation of the desired salt, through the action of the corresponding base or acid, preferably in a final step, into the process according to the invention.

The process according to the invention is illustrated in SCHEME 1 hereinafter, in which R, R" and R'b are as defined for the compounds of formulae (II), (III) and (I).

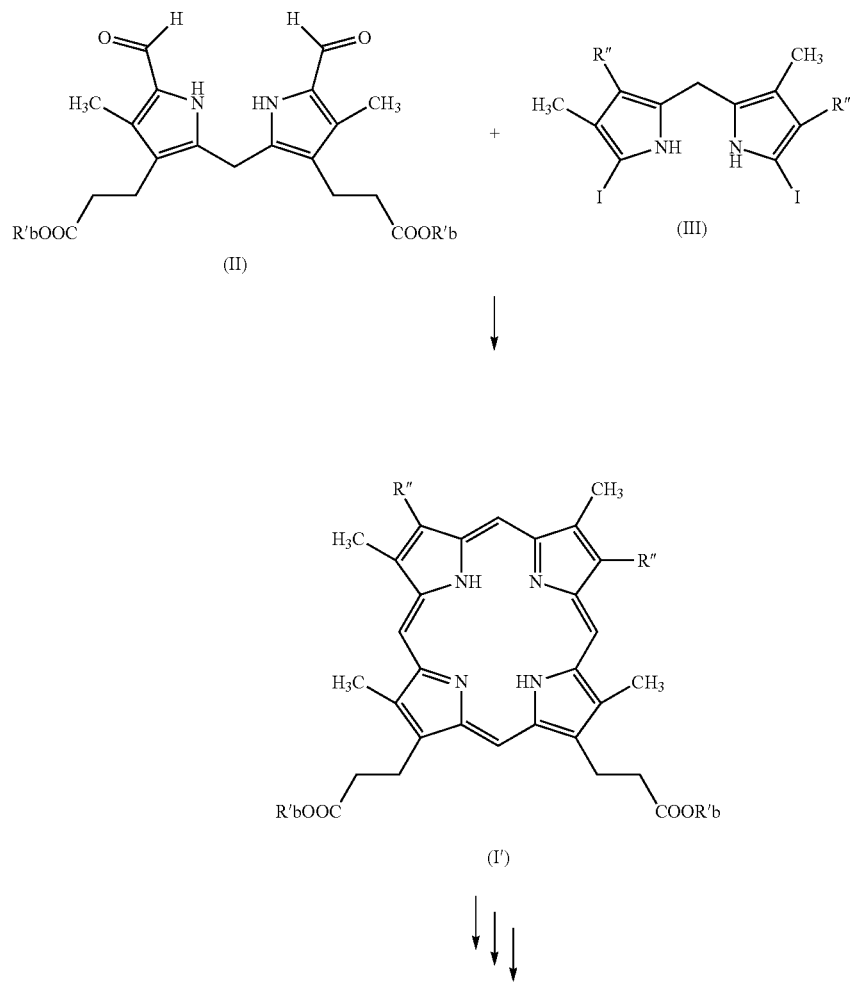

SCHEME 1

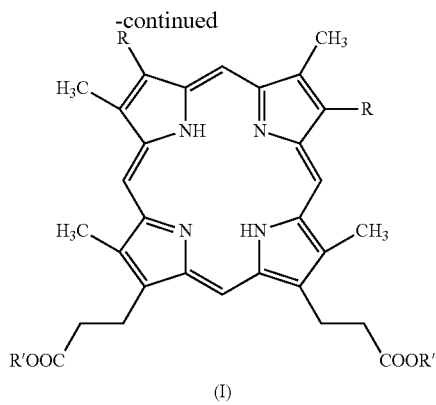

(I)

Depending on the nature of the group R, the coupling can be carried out between a compound (II) and a compound (III) in which R''=R: this is, for example, the case when R=H, —CH$_2$—CH$_3$, —CH(OH)CH$_3$, —C(O)CH$_3$ or —CH$_2$CH$_2$COOR'a, with R' a being a hydrogen atom or a methyl, ethyl, n-propyl or i-propyl group.

If the group R'b=R', the compound (I') directly obtained after the condensation step is the desired compound (I), without any additional step being necessary. If the compound R'b is other than R', which is the case when R'=H or else in cases where the acid functions are in the form of a salt, for example, with an alkali metal such as Na$^+$ or K$^+$, the coupling is followed by deprotection of the acid function by elimination of the group R'b, in order to convert the compound (I') to compound (I).

The coupling can also be carried out with a compound (III) in which R'' is a precursor of R (also referred to herein as a group that is precursor of R). The expression "precursor of R" and "group that is a precursor of R" are intended to mean a group which, after one or more chemical reactions, gives the desired group R. By way of example of such precursor groups, in particular for the —CH$_2$=CH$_2$ group, mention may, for example, be made of the —C(O)CH$_3$, —CH(OH)CH$_3$, —CH$_2$CH$_2$OH, —CH$_2$CH$_2$OC(O)CH$_3$ or —CH$_2$CH$_2$Cl groups, —C(O)CH$_3$ and —CH(OH)CH$_3$ groups being particularly preferred. The coupling with the compound (III) gives a compound (I'):

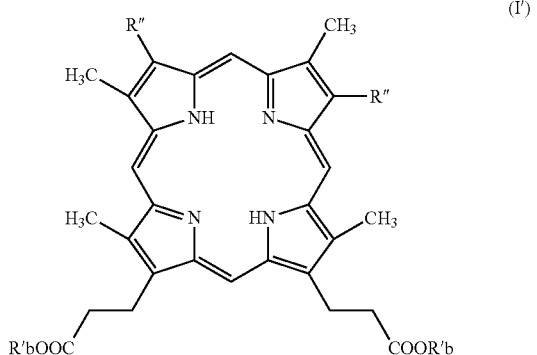

(I')

in which R'' is a group that is a precursor of R. The group that is a precursor of R must then be converted so as to give the desired group R, in one or more steps. This is, for example, the case for the preparation of the compounds of formula (I) in which R=—CH=CH$_2$, —CH$_2$—CH$_3$, —CH(OH)CH$_3$ or H. In the case of such groups, one of the methods consists in carrying out the coupling with a compound (III) in which R''=—C(O)CH$_3$, which is subsequently converted, after the step of condensation between the compounds (II) and (III), so as to obtain the desired group R.

Moreover, depending on the nature of the group R', the coupling can be carried out between a compound (III) and a compound (II) in which R'=R'b. On the other hand, in the case where R'=H, or else in cases where the acid functions are in the form of a salt, for example, with an alkali metal such as Na$^+$ or K$^+$, the coupling is followed by deprotection of the acid function by elimination of the group R'b.

When, after the step of coupling between the compounds (II) and (III), the two steps, i.e. the conversion of the groups R'' to R and the elimination of the groups R'b, are necessary, the deprotection of the acid function can take place before or after the conversion of the groups R'' to R. It is, however, preferable to eliminate the groups R'b after the conversion of the group R'' to R, since ester functions improve the solubility in the reaction solvents.

Unlike the MacDonald method of the prior art, the step of condensation between the compounds (II) and (III) is carried out in the absence of metal, salt or metal derivative, liable to complex with the porphyrin (I') formed.

In the context of the invention, for the preparation of a compound of formula (I) in which R is a hydrogen atom or a group selected from: —CH$_2$—CH$_3$, —CH(OH)CH$_3$, —C(O)CH$_3$ and —CH$_2$CH$_2$COOR' a with R' a being a hydrogen atom or a methyl, ethyl, n-propyl or i-propyl group, the coupling may be carried out either with a compound (III) in which R'' is the final group R, or with a compound (III) in which R'' is a group that is a precursor of the final group R.

For the preparation of a compound of formula (I) in which R is a —CH=CH$_2$ group, use will preferably be made of:
a step of condensation, in an acidic medium, between a dipyrromethane of formula (II):

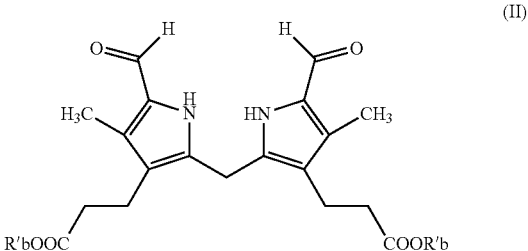

(II)

in which R'b is as defined above for (I), and a dipyrromethane of formula (III):

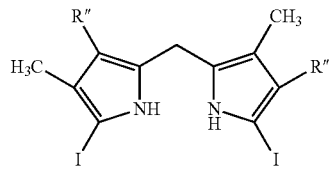

in which R" is a group that is a precursor of R, for example a —CH(OH)CH₃ or —C(O)CH₃ group,
followed by conversion of the groups R" to R,
and when R'=H, by elimination of the groups R'b so as to form a —COOH groups, optionally in the form of a salt.

The process according to the invention is particularly suitable for the synthesis of protoporphyrin and of salts thereof, in particular its sodium salt of formula (IC.2, 2Na):

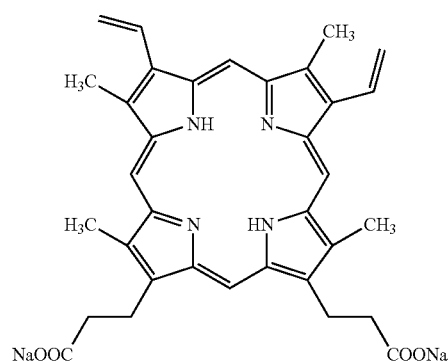

In the case of the preparation of a compound of formula (IC):

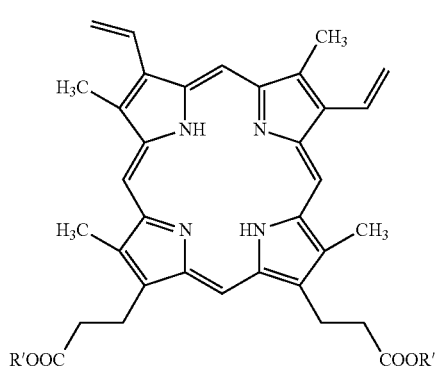

in which R' is as defined for (I), or a salt thereof, for example, with an alkali metal, a coupling is advantageously carried out between a pyrromethane of formula (II):

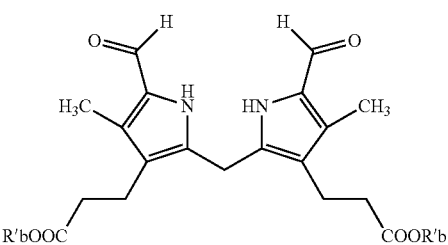

in which R'b is as defined for (I), and is preferably a methyl group,
and a dipyrromethane of formula (IIIa):

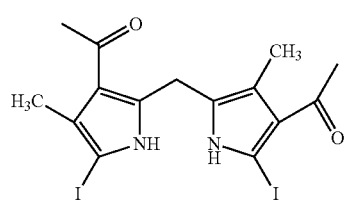

so as to form the compound of formula (Ia):

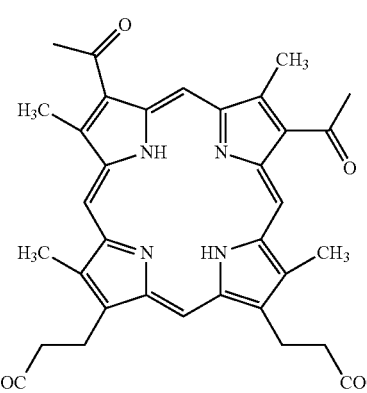

in which R'b is as defined for (I), and is preferably a methyl group,
followed
by reduction of the —C(O)CH₃ function, resulting in the formation of the porphyrin of formula (Ib):

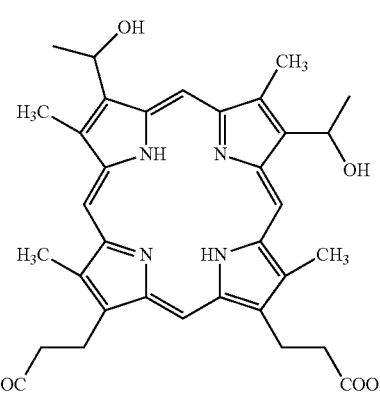

in which R'b is as defined for (I), and is preferably a methyl group, followed by an elimination reaction that converts the groups —CH(OH)CH₃ to —CH=CH₂, and, in the case where R' is a hydrogen atom, by a step of deprotection of the —COOH function by hydrolysis, or, in the case where the compound (IC) that it is desired to form is in the form of a salt with an alkali metal, by a saponification step.

It should be noted that, in the context of the invention, the compound of formula (Ib) comprises two asymmetrical carbons and can be in the form of a mixture of isomers or of a pure isomer.

This process for preparing the compounds of formula (IC) is illustrated in SCHEME 2 below in which R'b is as defined for the compounds of formula (II):

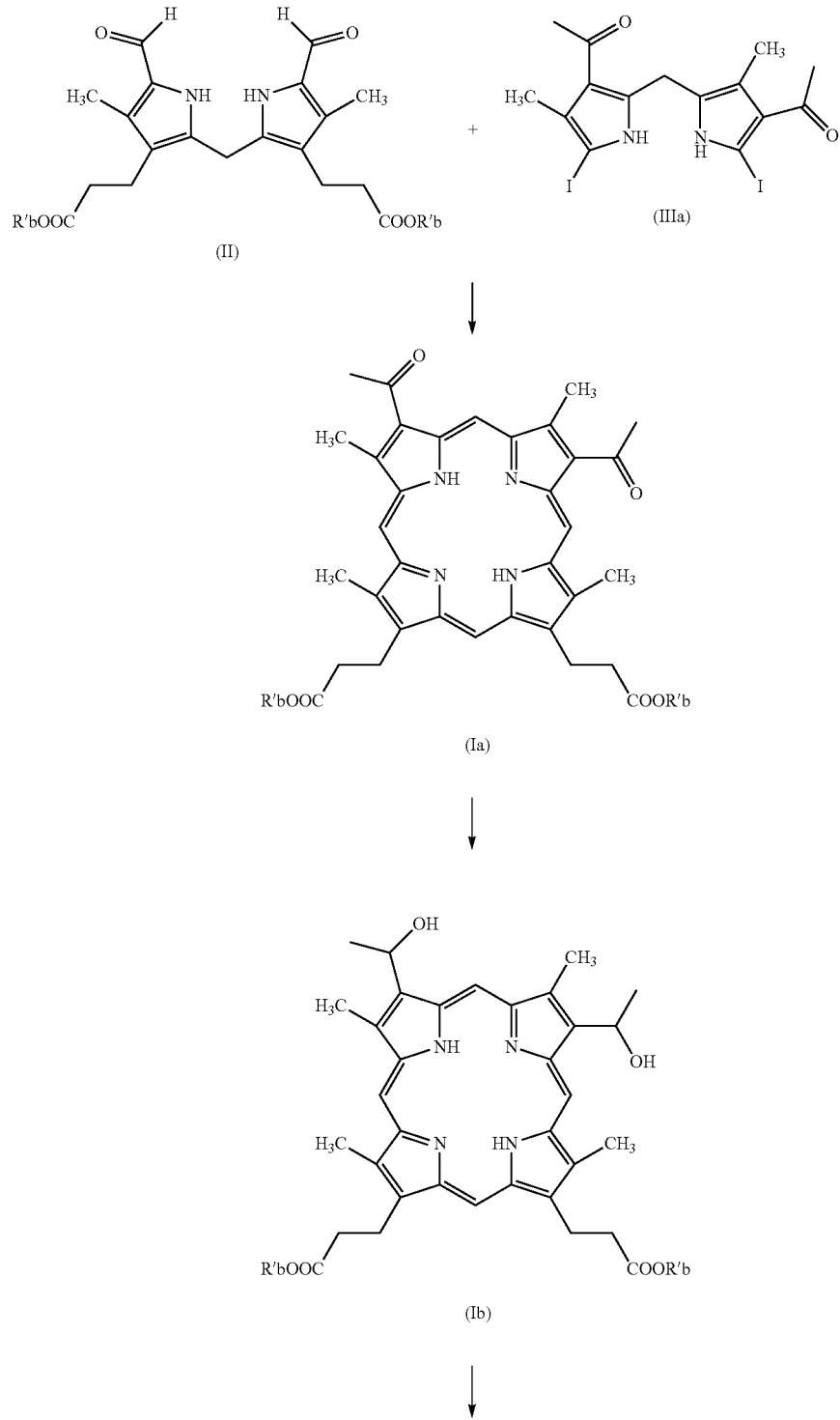

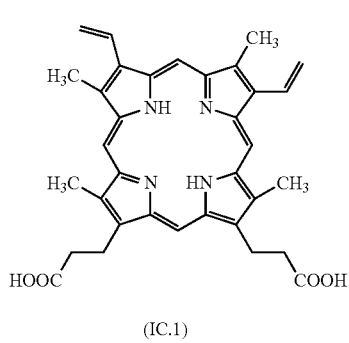

(IC.1)

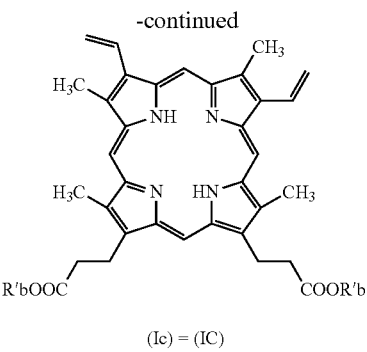

(Ic) = (IC)

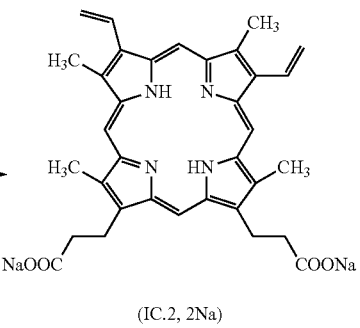

(IC.2, 2Na)

in which R'=R'b

In the case of the preparation of protoporphyrin IX in the form of the sodium salt of formula (IC.2, 2Na):

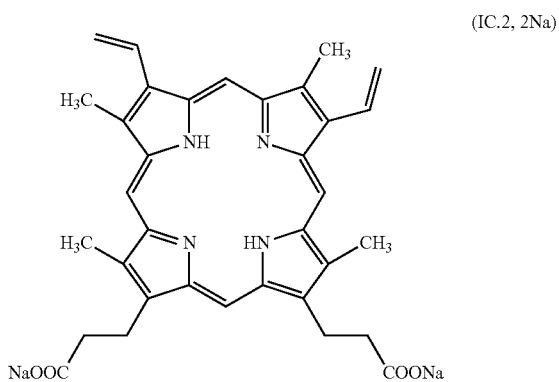

(IC.2, 2Na)

the last step of the process consists of the saponification of the two —COOR'b groups of the compound of formula.

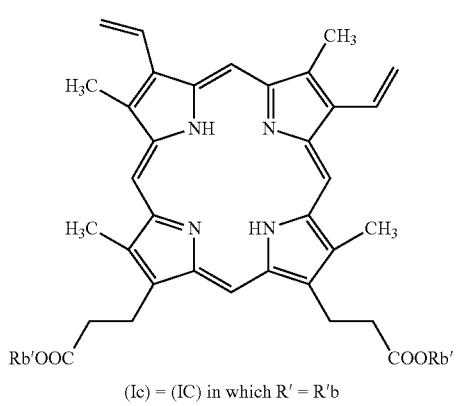

(Ic) = (IC) in which R' = R'b in which R'b is as defined for (I), and is preferably a methyl group. This saponification step can be carried out by the action of sodium hydroxide, in the presence of methanol. For example, the saponification step is carried out in dichloromethane at reflux. According to an unpreferred variant, it could also be envisaged that this saponification step be carried out after the coupling between the compounds (II) and (IIIa), but before the desired —CH=CH₂ group is obtained.

The condensation reaction between the two pyrromethanes (II) and (III) or (IIIa) is preferably carried out in the presence of an acid selected from the carboxylic acids, trifluoroacetic acid, hydrochloric acid, trichloromethanesulfonic acid, methanesulfonic acid, trifluoromethanesulfonic acid, tetrafluoroboric acid, hydrobromic acid and hydriodic acid. The acid is preferably a strong acid, preferably trifluoroacetic acid or trichloromethanesulfonic acid. The acid is preferably used in excess relative to the pyrromethane (II), for example 2 mol equivalents of acid per mol equivalent of pyrromethane (II).

Advantageously, the condensation reaction between the two pyrromethanes (II) and (III) or (IIIa) is carried out in the presence of a desiccating agent, intended to take up water molecules. By way of desiccating agent, mention may be made of anhydrides, molecular sieves and sulfuric acid, acetic anhydride being preferred. In the case of the use of acetic anhydride, the latter is preferably present in an excess, for example, of at least 10, preferably of at least 50 mol equivalents relative to the pyrromethane (II) (or per one mol equivalent of pyrromethane (II)).

It will also be advantageous to carry out the condensation with substantially one equivalent or a slight excess of pyrromethane (II), relative to the pyrromethane (III) or (IIIa). By slight excess, it is meant that the condensation between pyrromethane (II) and pyrromethane (III) or (IIIa) is carried out at a molar ratio between these two components of 1:1.2, or preferably of 1:to 1.1.

The condensation reaction between the two pyrromethanes (II) and (III) or (II) and (IIIa) is, for example, carried out at a temperature of from 10 to 50° C., preferably from 20 to 25° C., in a protic solvent, such as acetic acid.

The reactions following the coupling, that make it possible to obtain the desired group R, make use of known methods.

The elimination reaction that converts the groups —CH(OH)CH₃ to —CH=CH₂ is advantageously carried out in the presence of an acid halide, preferably an acid chloride such as benzoyl chloride. For example, the elimination reaction that converts the groups —CH(OH)CH₃ to —CH=CH₂ is carried out in an aprotic polar solvent such as DMSO (dimethyl sulfoxide), acetone or preferably DMF (dimethyl formamide), preferably at a temperature of from 50 to 200° C. for a period of 30 minutes to 3 hours, and preferably at a temperature of from 80 to 120° C. for a period of the order of one hour.

The reduction of the —C(O)CH₃ function to —CH(OH)CH₃ is advantageously carried out in the presence of a hydride, preferably a borohydride such as NaBH₄ or BH₃. Preferably, the reduction of the —C(O)CH₃ function is carried out in dichloromethane in the presence of methanol, for example at a temperature of between 0 and 60° C., preferably between 20 and 30° C.

Subsequently, the compound of formula (I) in which R=—CH=CH₂ can be subjected to other chemical reactions, in order to obtain other groups R. The compound of formula (I) in which R=—CH₂—CH₃, for example, can be obtained from the corresponding compound of formula (I) in which R=—CH=CH$_2$ by catalytic hydrogenation. For example, use may be made of the technique described in Tetrahedron Letters 2006, 47(29), 5119-22, which uses a RuCl$_3$ catalyst in AcNMe$_2$ at a temperature of the order of 80°.

Similarly, the compound of formula (I) in which R=H can be obtained from the corresponding compound of formula (I) in which R=—C(O)CH$_3$, by intermediately forming the compound of formula (I) in which R=—CH(OH)CH$_3$, which is subsequently deacetylated by the action of BF$_3$ in the presence of HS—(CH$_2$)$_2$—SH, for example using the method described in JOC, 1983, 48(24), 4779-81 or J. Chem. Soc, Chemical Communications, 1981, (6), 253-4.

According to one of its variants, the process according to the invention can therefore be implemented for the preparation of the compounds of formula (IA):

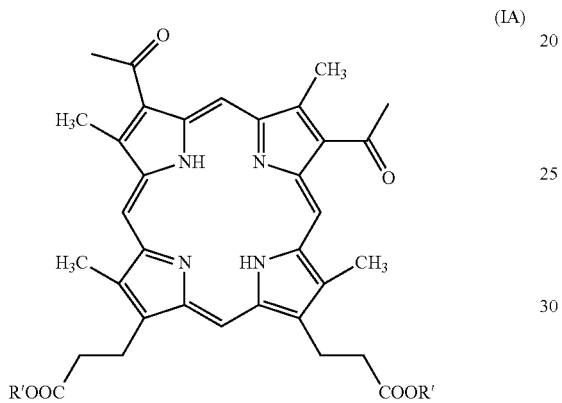

(IA)

in which R' is as defined for (I), or a salt thereof, for example, with an alkali metal,
by coupling the pyrromethane of formula (II):

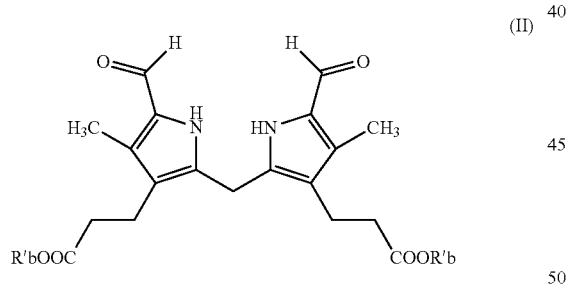

(II)

in which R'b is as defined above for (I), and is preferably a methyl group,
with a dipyrromethane of formula (IIIa):

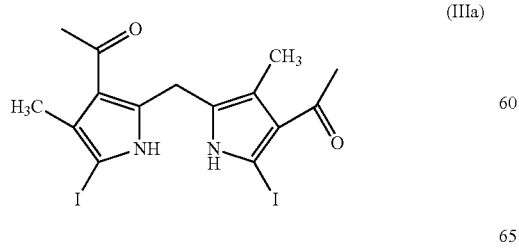

(IIIa)

followed, in the case where R' is a hydrogen atom, by a step of deprotection of the —COOH groups by hydrolysis, and/or, optionally in the case where it is desired to form the compound (Ia) in the form of a salt with an alkali metal, by a saponification step.

The process according to the invention can also be implemented for the preparation of the compound of formula (IB):

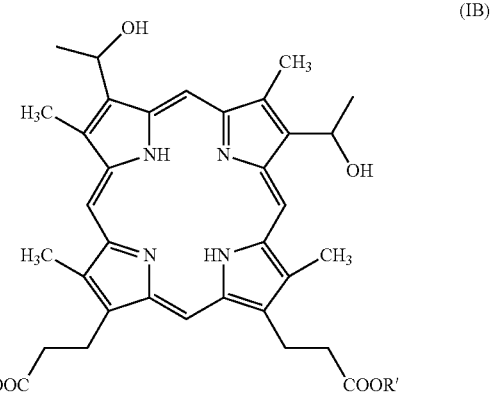

(IB)

in which R' is as defined for (I), or a salt thereof, for example, with an alkali metal,
by coupling the pyrromethane of formula (II):

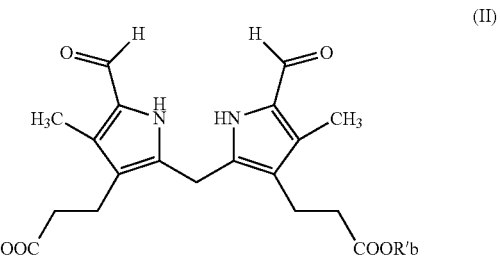

(II)

in which R'b is as defined above for (I), and is preferably a methyl group,
with a dipyrromethane of formula (IIIa):

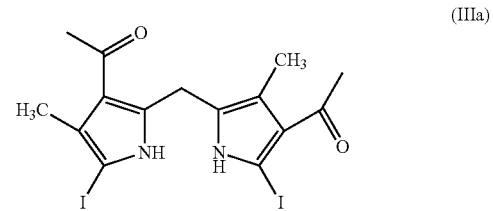 [SMILES: CC(=O)c1c(I)[nH]c(Cc2[nH]c(I)c(C)c2C(C)=O)c1C]

(IIIa)

so as to form a compound of formula (Ia):

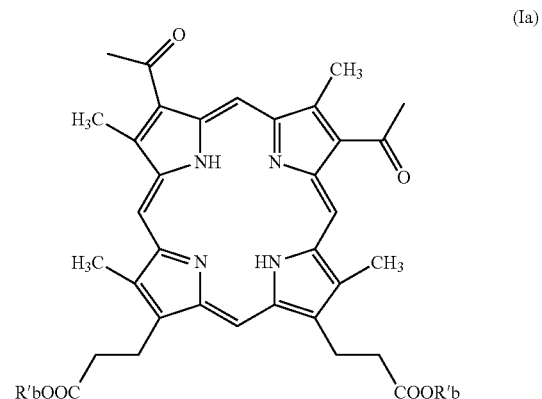

(Ia)

in which R'b is as defined above for (I), and is preferably a methyl group, followed by reduction of the —C(O)CH₃ function, so as to form the —CH(OH)CH₃ function, and, in the case where R' is a hydrogen atom, by a step of deprotection of the —COOH function by hydrolysis, and/or, in the case where it is desired to form a compound (IB) in the form of a salt with an alkali metal, by a saponification step.

The compound (II) in which R'b=Me is a known compound, just like the compounds (II) in which R'b is an ethyl or propyl group (JCS Perkin I, 1974, 1188-1194 and 1771-1781). For their synthesis, reference may, for example, be made to Austral. J. Chem. 1969, 22, 229, JCS, Chem. Comm. 1985, (8), 470-1, Org. Bioorg. Chem. (1972-1999), 1987, (2), 265-76, and J. Porphyrins and Phtalocyamines, 2002, 6 (9+10), 607-16.

On the other hand, the pyrromethanes of formula (III):

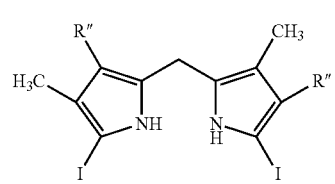

(III)

in which R" is a group R selected from a hydrogen atom or a group selected from: —CH═CH₂, —CH₂—CH₃, —CH(OH)CH₃, —C(O)CH₃ and —CH₂CH₂COOR'a, with R'a being a hydrogen atom or a methyl, ethyl, n-propyl or i-propyl group, are new compounds and are an integral part of the invention.

Among the compounds of formula (III), mention may be made of those in which R" is a group that is a precursor of —CH═CH₂ selected from: —C(O)CH₃, —CH(OH)CH₃, —CH₂CH₂OH, —CH₂CH₂OC(O)CH₃ and —CH₂CH₂Cl.

The conversion of the —CH₂CH₂OH, —CH₂CH₂OC(O)CH₃ or —CH₂CH₂Cl group to —CH═CH₂ is carried out according to the usual methods of elimination well known to those skilled in the art. For example, the —CH₂CH₂Cl group can be treated by the action of alcoholic potassium hydroxide as described in J. C. S. Perkin 1, 1974, 1771-1781.

By way of example of such compounds, mention may be made of the pyrromethane of formula (IIIa):

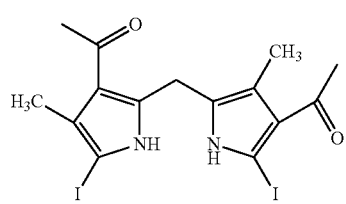

(IIIa)

The compounds (III) can be prepared according to SCHEME 3 hereinafter:

SCHEME 3

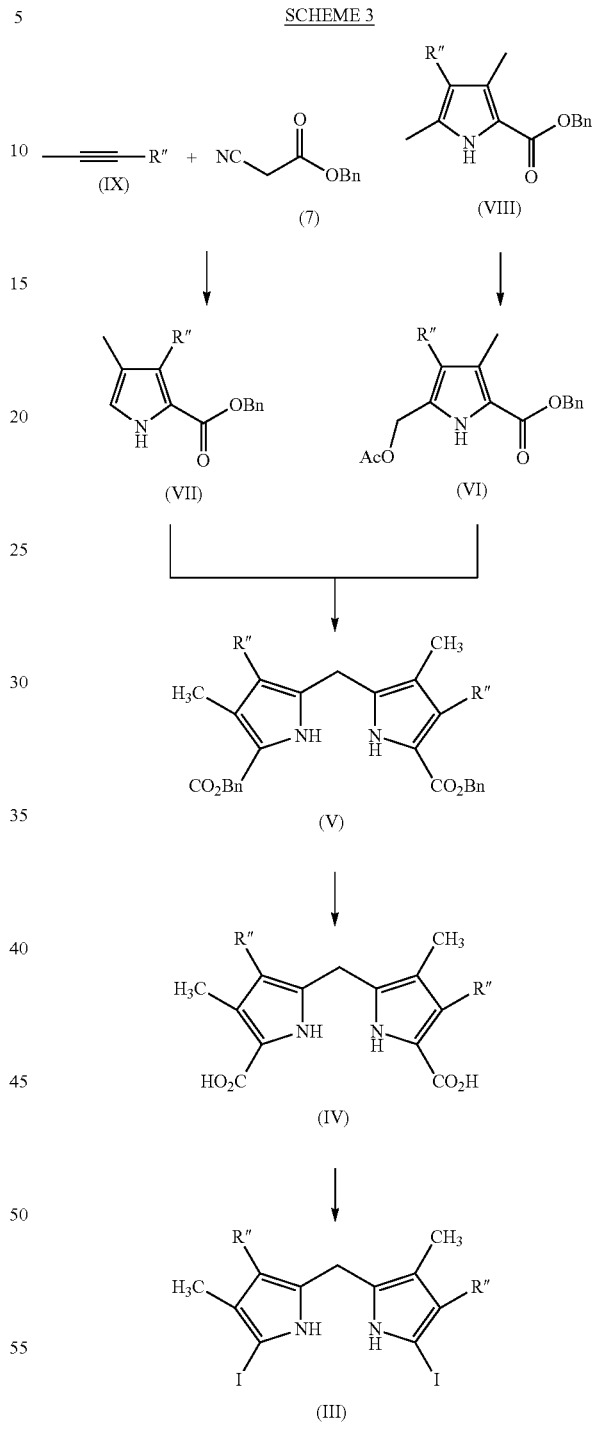

In the case where R" is a —C(O)CH₃ group, the compound (IX) is, for example, prepared by reaction of trimethylsilylpropyne and acetyl chloride, in the presence of aluminum trichloride.

The coupling between the compounds (VII) and (VI) is preferably carried out in an acidic medium, for example in the presence of TFA, HCl, MeSO₃H, SnCl₄ or HBF₄, and advantageously in the presence of HBF₄ or of CF₃SO₃H. For example, the coupling is carried out in a solvent such as acetic acid, or preferably dichloroethane, for example at a temperature of between 50 and 150° C., in particular of the order of 90 to 100° C., for 1 to 12 hours.

The production of the compound (IV) by debenzylation of the compound (V) is, for example, carried out by catalytic hydrogenation. By way of illustration, a metal catalyst, such as a nickel-based, platinum-based or preferably palladium-based catalyst, can be used.

The following compounds of formulae (VIIa), (Va), (IVa) (compounds VII, V and IV, respectively, in which R"=—C(O)CH$_3$):

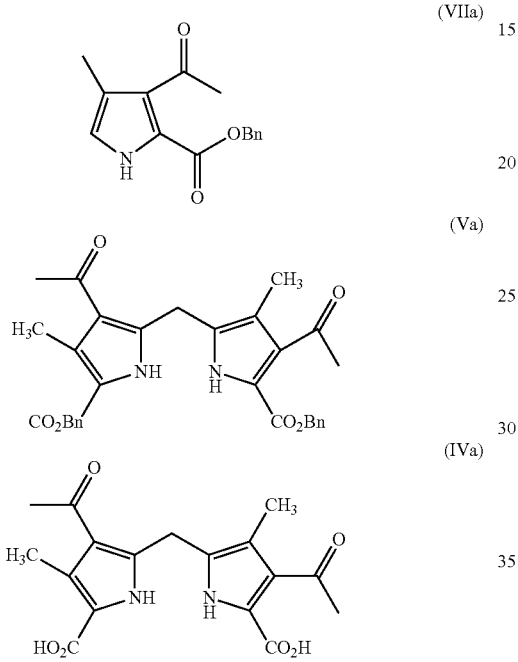

are also novel intermediates that are an integral part of the invention.

For the preparation of the compound (IV) in which R"=—CH$_2$CH$_2$COOR' a with R'a as defined for (I), reference may be made to JCS, Perkin Trans 1 Org and Bioorg Chem. 1987 (2), 299-305. The compound (IV) in which R"=—CH$_2$CH$_3$ is, for its part, described in Zhurnal Obshcheikhimii 1966, 36(7), 1208-10.

The present invention also relates to a process for preparing a porphyrin of formula (I), optionally in the form of a salt:

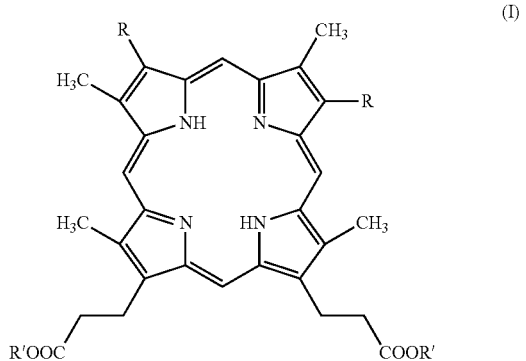

in which:
R is a hydrogen atom or a group selected from: —CH=CH$_2$, —CH$_2$—CH$_3$, —CH(OH)CH$_3$, —C(O)CH$_3$ and —CH$_2$CH$_2$COOR'a, with R' a being a hydrogen atom or a methyl, ethyl, n-propyl or i-propyl group,
R' is a hydrogen atom or a group R'b selected from methyl, ethyl, n-propyl or i-propyl,
in the form of a metal complex, for example iron, gallium, nickel, zinc, palladium, cobalt, calcium or magnesium, in which a step of complexation of a porphyrin, formed after the step of condensation between the compounds (II) and (III) or (IIIa), is carried out, by the action of the selected metal or of a metal derivative or salt of the selected metal.

Such complexes correspond, in particular, to the following formula (I"):

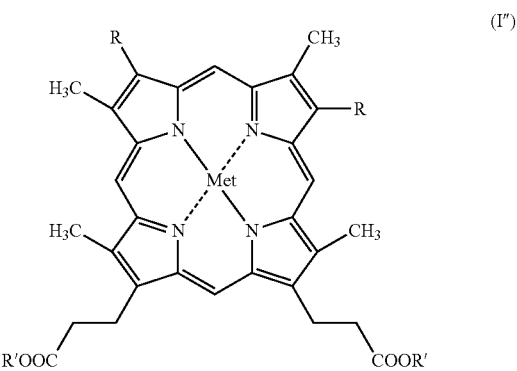

in which:
R is a hydrogen atom or a group selected from: —CH=CH$_2$, —CH$_2$—CH$_3$, —CH(OH)CH$_3$, —C(O)CH$_3$ and —CH$_2$CH$_2$COOR'a, with R' a being a hydrogen atom or a methyl, ethyl, n-propyl or i-propyl group,
R' is a hydrogen atom or a group R'b selected from methyl, ethyl, n-propyl or i-propyl, and
Met is a divalent metal M(II) or a metal salt of a trivalent metal M(III)X, with X being Cl or OH and M being iron, gallium, nickel, zinc, palladium, cobalt, calcium or magnesium.

The porphyrin of formula (I) or the porphyrin of formula (I') obtained, in the process according to the invention, can be reacted with a metal or a metal salt or the hydroxide metal of the type chloride, hydroxide, acetate or sulfate in particular, the metal being, for example, chosen from iron, gallium, nickel, zinc, palladium, cobalt, calcium or magnesium, so as to obtain the porphyrin of formula (I) in the form of a metal complex. This metalation necessarily takes place after the coupling of the pyrromethanes (II) and (III) or (IIIa).

The complexation step is preferably carried out as a final step, on the porphyrin of formula (I), optionally in the form of a salt. For the formation of such complexes, reference may be made to the following publications, which describe the formation of metal complexes in the case where R" is a —CH=CH$_2$ group, or to known methods of complexation for obtaining heme, hemin and hematin, these methods being adapted to the various groups R and R' as defined for all the compounds of formula I:

Journal of Photochemistry and Photobiology, A: Chemistry, 172(1), 55-61, 2005, which describes the formation of the following complex:

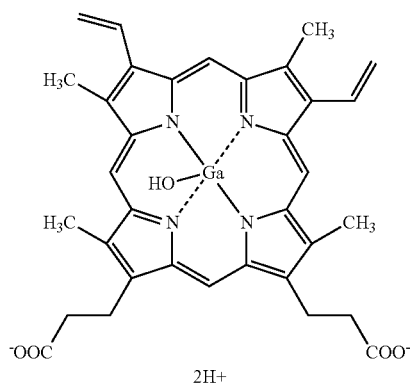

2H+ by the action of GaCl$_3$, followed by hydrolysis with potassium hydroxide in methanol, it being possible for this method to be adapted in a similar manner to the formation of hematin, by the action of FeCl$_3$, Journal of Molecular Catalysis A: Chemical, 235(1-2), 185-193, 2005, which describes the formation of the following complex:

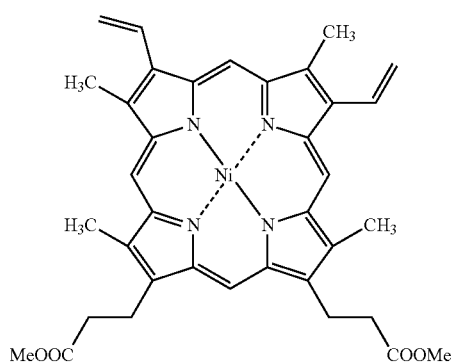

by the action of Ni(OAc)$_2$, in DMF.

Journal of Molecular Catalysis A: Chemical, 235(1-2), 185-193, 2005, which describes the formation of the complex C:

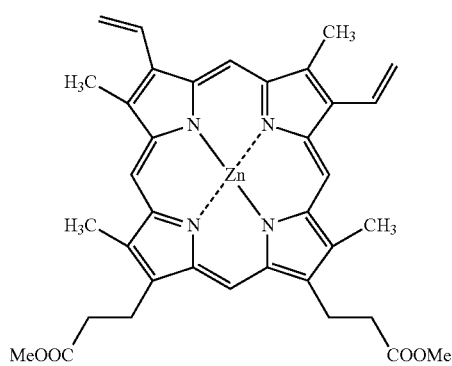

by the action of Zn(OAc)$_2$, in a methanol/trichloromethane mixture.

Faming Zhuanli Shenqing Gongkai Shuomingshu, 1418885, which describes the formation of the following complex:

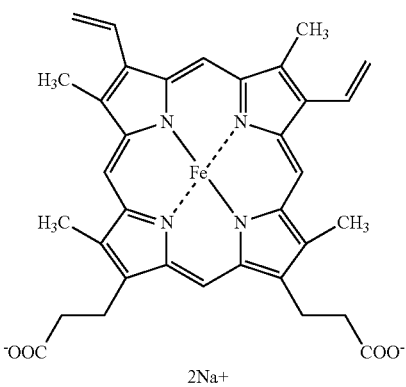

2Na+ by treatment with sulfuric acid, and then treatment with FeSO$_4$ followed by treatment with sodium hydroxide.

Tetrahedron Letters, 27(30), 3521-4, 1986, which describes the formation of the following complex:

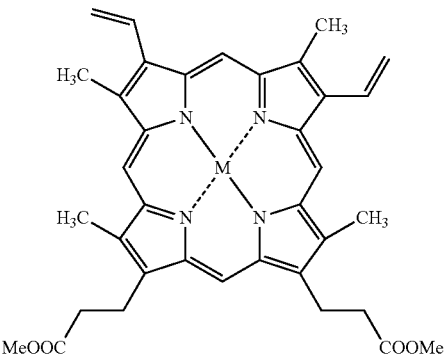

by the action of BF$_4^-$, Ph$_2$S$^+$ (CH$_2$Ph) in dichloromethane, followed by the action of PdCl$_2$ in the case where M=Pd, of NiCl$_2$ in the case where M=Ni, or of CoCl$_2$ in the case where M=Co, in methanol.

Journal of Organic Chemistry, 51(24), 4660-7, 1986, and Journal of Organic Chemistry, 51(5), 666-71, 1986, which describes the formation of the following complex:

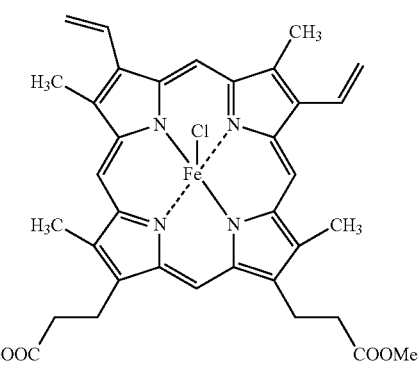

by the action of FeCl$_2$, in a dichloromethane/acetonitrile mixture under an inert atmosphere.

The examples and preparations hereinafter make it possible to illustrate the invention.

SCHEME 4 hereinafter summarizes the various compounds prepared and the steps of the process used in the preparations and examples.

The following abbreviations are used.
Bn=benzyl, Et=ethyl, Ac=-C(O)Me, Me=methyl
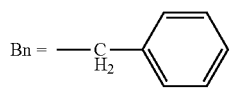
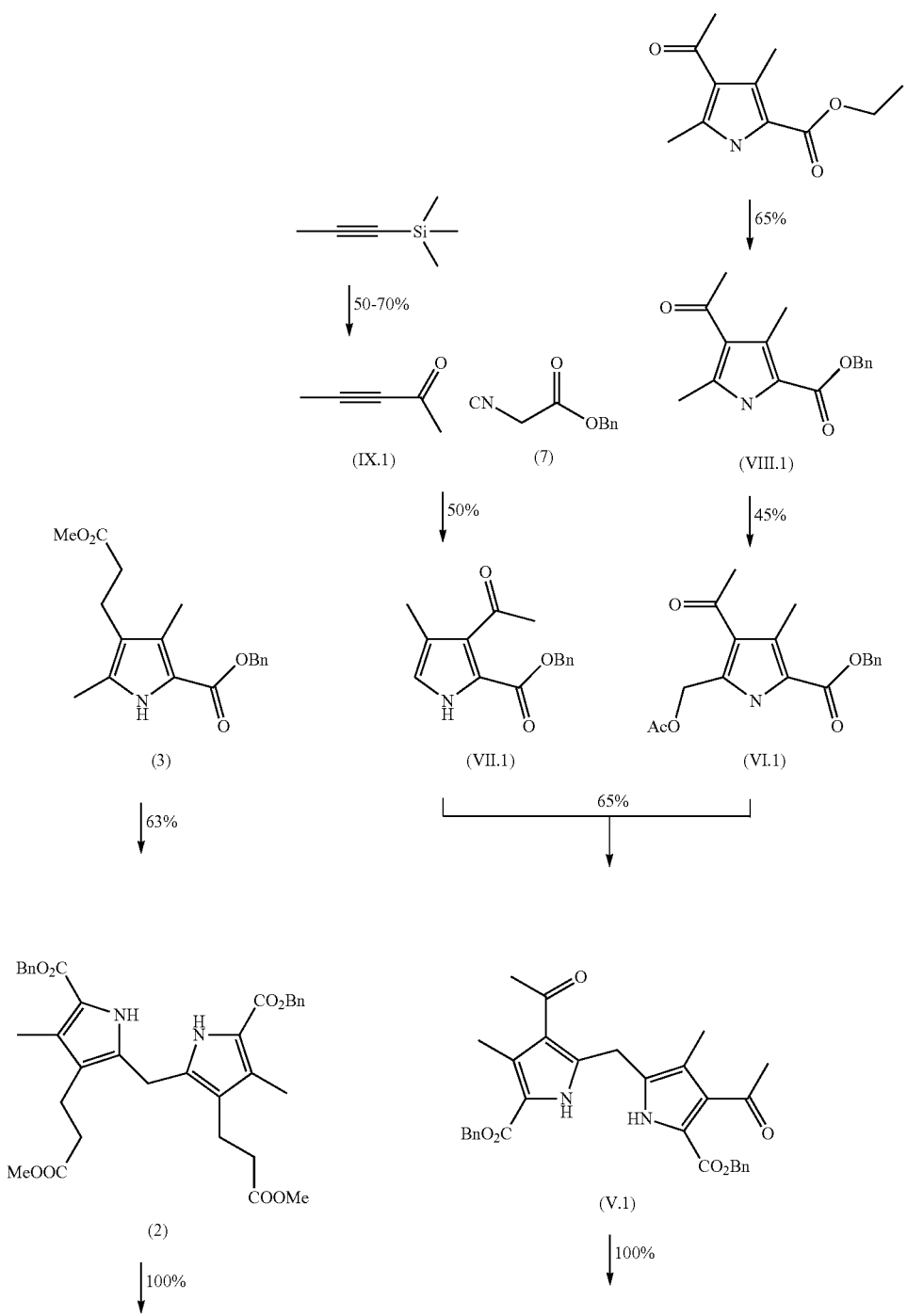
Scheme 4

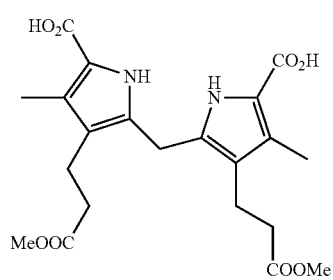
(1)
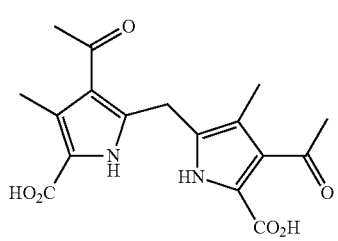
(IV.1)
↓ 83%
↓ 90%
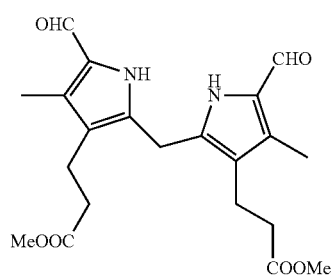
(II.1)
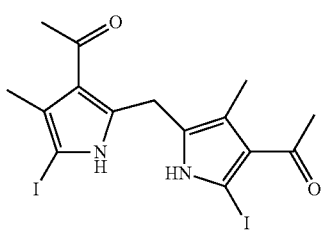
(IIIa)
55% ↓
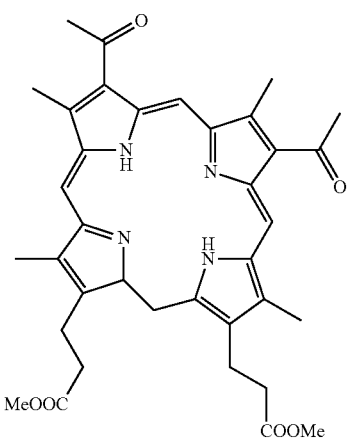
(Ia.1)
→ 95%
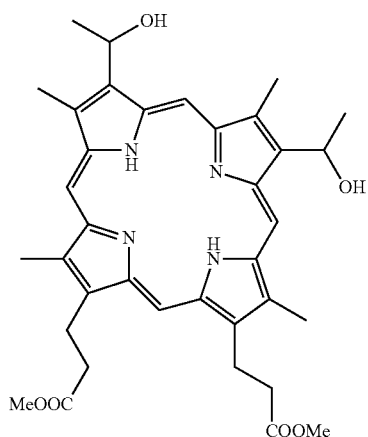
(Ib.1)
→ 70%

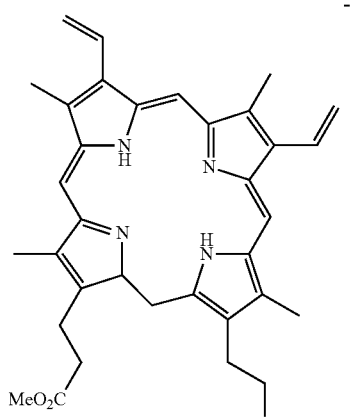

(Ic.1)

90% ↓

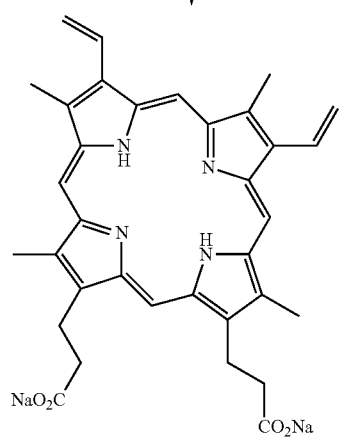

(IC.2,2Na)

Preparation 1

Synthesis of the Pyrrole of Formula (3):

(3)

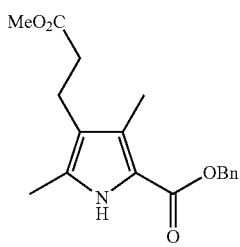

a) Preparation of the Compound of Formula (6):

(6)

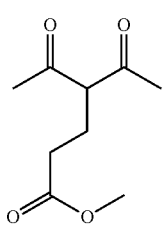

A 4.5 l Keller round-bottomed flask equipped with a reflux condenser, a thermometer, a dropping funnel and an argon conduit is loaded with ethanol (2 l). At ambient temperature, sodium (2.2 g) is gradually dissolved so as to give a clear solution which is cooled to 0° C. Acetyl acetonate (500.0 g, 5.0 mol) is added dropwise in 10 min, which results in gas being given off 430 g of methyl acrylate are added dropwise to the light yellow solution at 0° C. in 10 min, which results in gas being given off. The reaction mixture is heated to ambient temperature and is then refluxed for 1 h. The conversion is followed by HPLC. The mixture is cooled to ambient temperature. Acetic acid (3 ml) is added and the ethanol is eliminated by distillation under reduced pressure. The distillation of the crude mixture (95-105° C., 2.5 mbar) gives a light yellow solution (747.8 g, 80%). The $^1$H NMR analysis shows that the crude product is an ~1/1 mixture of compound (6) and of methyl 5-oxohexanoate.

b) Preparation of the Compound of Formula (5):

(5)

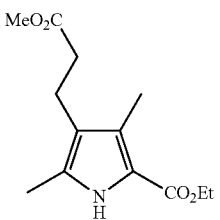

A 4.5 l Keller round-bottomed flask equipped with a reflux condenser, a thermometer, a dropping funnel and an argon conduit is loaded with acetic acid (1.30 l) and refluxed. A solution of a mixture of compound (6) (248.71 g, 1.34 mol) and of dimethyl aminomalonate hydrochloride (367.50 g, 1.74 mol) in acetic acid (0.85 l) is added dropwise to the mixture at reflux, over 1 h. The mixture is again refluxed for 2.5 h. The conversion is followed by HPLC. The reaction mixture is cooled to ambient temperature and the acetic acid is eliminated by distillation under reduced pressure. The dark crude product is triturated with water (4.5 l), which is added slowly, portionwise. The mixture is mechanically stirred for a further 1 h and is then filtered, and the filtration cake is washed with water (1 l). The recrystallization of the dark gray crude product is carried out from ethanol/water (350/350 ml) by refluxing and then cooling to 10° C. The precipitate is isolated by filtration and washed with ethanol/water (4×100/100 ml). The product is dried under reduced pressure at ambient temperature, to give the compound (5) (95.00 g, 28%) in the form of a light purple-colored solid.

$^1$H NMR (300 MHz, CDCl$_3$): 1.34 (t, CH$_3$), 2.21 (s, CH$_3$), 2.27 (s, CH$_3$), 2.43 (t, CH$_2$), 2.70 (t, CH$_2$), 3.66 (s, CH$_3$), 4.29 (q, CH$_2$), 8.60 (broad singlet, NH$_2$).

c) Preparation of the Compound of Formula (4):

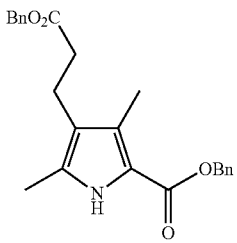

(4)

A 2.5 l Keller round-bottomed flask equipped with a reflux condenser/distillation head, a thermometer, a dropping funnel and an argon conduit is loaded with a solution of compound (5) (95.00 g, 0.38 mol) in benzyl alcohol (685 ml) and heated to 120° C., which results in the azeotropic removal of minor amounts of water. The mixture is then heated to 190° C. The dropping funnel is loaded with a separately prepared solution of sodium (3 g) in benzyl alcohol (70 ml). This solution is added in 5 ml portions, which results in a vigorous reflux of the reaction mixture. The resulting methanol and ethanol are removed by semi-continuous distillation. The conversion is followed by HPLC. The reaction mixture is cooled to 150° C. and then transferred into a mixture of methanol (0.85 l), water (0.54 l) and acetic acid (10 ml). At 30° C., crystallization takes place rapidly. The mixture is stirred again at ambient temperature for 1 h. The product is isolated by filtration. The product is dried under reduced pressure, to give the compound (4) (113.30 g, 77%) in the form of an off-white solid.

$^1$H NMR (300 MHz, CDCl$_3$): 2.16 (s, CH$_3$), 2.27 (s, CH$_3$), 2.47 (t, CH$_2$), 2.71 (t, CH$_2$), 4.70 (s, CH$_3$), 5.08 (s, CH$_2$), 5.28 (s, CH$_2$), 7.40 (m, 10H), 8.60 (broad singlet, NH$_2$).

d) Preparation of the Compound of Formula (3):

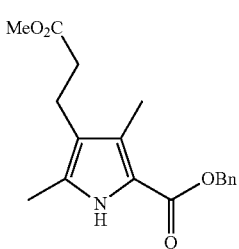

(3)

A 2.5 l Keller round-bottomed flask equipped with a reflux condenser, a thermometer, a dropping funnel and an argon conduit is loaded with a solution of sodium (2.8 g) in methanol (710 ml). At ambient temperature, a solution of compound (4) (111.00 g, 0.28 mol) in THF (430 ml) is added dropwise in 10 min. The mixture is stirred for a further 1 h. The conversion is followed by HPLC. After the addition of acetic acid (7 ml), the volatile products are removed under reduced pressure. The crude viscous product is dissolved in ethanol (490 ml) and water (280 ml) is added. The resulting mixture is stirred for 1 h at 0° C. and the precipitated product is isolated by filtration. The product is washed with ethanol/water (250/250 ml) and dried under reduced pressure, to give the compound (3) (53.31 g, 60%) in the form of a white solid.

$^1$H NMR (300 MHz, CDCl$_3$): 2.25 (s, CH$_3$), 2.31 (s, CH$_3$), 2.45 (t, CH$_2$), 2.71 (t, CH$_2$), 3.67 (s, CH$_3$), 5.30 (s, CH$_2$), 7.40 (m, 5H), 8.60 (broad singlet, NH).

RP-HPLC:

HP Hypersil BDS-C 18, 125×4 mm, 25° C.

Solvents with 0.1% of TFA: acetonitrile (ACN)-water: from 1 to 100% of ACN for 10 min, then 2 min with 100% of ACN Flow rate: 1 ml/min, detection at 220 nm Sample: 1 mg/1.5 ml of ACN Rt: 8.53 min (>98%)

Preparation 2

Preparation of the Compound of Formula (VII.1):

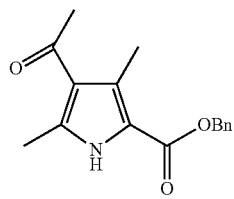

(VIII.1)

A 2.5 l Keller round-bottomed flask equipped with a reflux condenser/distillation head, a thermometer, a dropping funnel and an argon conduit is loaded with a solution of ethyl 4-acetyl-3,5-dimethylpyrrole-2-carboxylate (commercial product, Alpha Aesar, Karlsruhe, Germany, product No. A 17365) (146.00 g, 0.70 mol) in benzyl alcohol (1.00 l) and heated to 120° C., which results in the azeotropic removal of minor amounts of water. The mixture is then heated to 190° C. The dropping funnel is loaded with a separately prepared solution of sodium (2 g) in benzyl alcohol (20 ml). This solution is added in 5 ml portions, which results in a vigorous reflux of the reaction mixture. The resulting methanol and ethanol are removed semi-continuously by distillation. The conversion is followed by HPLC. The reaction mixture is cooled to 150° C. and then transferred into a mixture of methanol (0.96 l), water (0.66 l) and acetic acid (12 ml). The mixture is cooled to −10° C. and again stirred at this temperature for 1.5 h. The precipitated product is isolated by filtration. The product is dried under reduced pressure, to give the compound (VIII.1) (124.40 g, 65%) in the form of an off-white solid.

$^1$H NMR (300 MHz, CDCl$_3$): 2.34 (s, CH$_3$), 2.40 (s, CH$_3$), 2.52 (s, CH$_3$), 5.23 (s, CH$_2$), 7.85 (m, 5H), 9.55 (broad singlet, NH)

Preparation 3

Preparation of the Compound of Formula (VI.1):

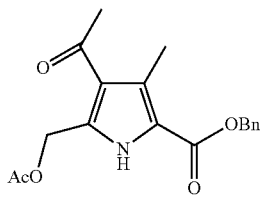

(VI.1)

A 2.5 l Keller round-bottomed flask equipped with a reflux condenser, a thermometer, a dropping funnel and an argon conduit is loaded with compound (VIII.1) (66.84 g, 0.25 mol), acetic acid (1.25 l) and sodium acetate (73.90 g, 1.51 mol). In order to obtain a clear solution, the mixture is heated to ~35° C. and then cooled to ambient temperature. Sulfuryl chloride (32.4 ml, 0.40 mol) is added in 2 h, while the reaction is carefully controlled toward the end of the addition, in order to minimize by-product formation due to overreaction. Additional amounts of sodium acetate (50.0 g) are added, at ambient temperature, and the mixture is again stirred at ambient temperature overnight. Water (500 ml) is added, to give a clear solution. After the addition of a 9-1 water-methanol mixture (4.5 l), the reaction mixture is again stirred at ambient temperature for 1 h with precipitation of the product. The product is isolated by filtration and dissolved by refluxing in ethyl acetate (220 m). The two-phase mixture is removed from the oil bath and methanol (200 ml) is added with stirring. After further stirring for 1 h at ambient temperature, the product begins to crystallize. Additional amounts of methanol (500 ml) are added and the mixture is stirred and cooled to −10° C. The product is isolated by filtration. The product is dried under reduced pressure, to give the compound (VI.1) (37.14 g, 45%) in the form of a white solid.

$^1$H NMR (300 MHz, CDCl$_3$): 2.07 (s, CH$_3$), 2.41 (s, CH$_3$), 2.53 (s, CH$_3$), 5.27 (s, CH$_2$), 5.31 (s, CH$_2$), 7.32 (m, 5H), 9.40 (broad singlet, NH).

RP-HPLC:

HP Hypersil BDS-C C18, 125×4 mm, 25° C.

Solvents with 0.1% of TFA: acetonitrile (ACN)-water: from 1 to 100% of ACN for 10 min, then 2 min with 100% of ACN Flow rate: 1 ml/min, detection at 220 nm Sample: 1 mg/1.5 ml of ACN Rt: 7.89 min (>94%)

Preparation 4

Preparation of the Compound of Formula (7):

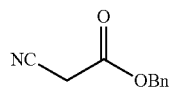

(7)

a) Preparation of the Compound of Formula (9):

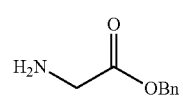

(9)

A 2.5 l Keller round-bottomed flask equipped with a reflux condenser, a thermometer, a dropping funnel and an argon conduit is loaded with glycine (80.00 g, 1.07 mol), benzyl alcohol (700 ml) and p-toluenesulfonic acid monohydrate (241 g, 1.27 mol). The thick white mixture is heated to 100° C., which results in the formation of a clear solution. The mixture is again stirred at 100° C. for 5 h. The mixture is cooled to ambient temperature. Diethyl ether (4 l) is added slowly, which results in precipitation of the product. The product is isolated by filtration, washed with ether (3×0.3 l) and dried under reduced pressure at 60° C. Because the conversion is incomplete, the white solid is taken up in toluene (2.3 l), and benzyl alcohol (0.3 l) and p-toluenesulfonic acid monohydrate (20 g) is added. The mixture is refluxed for 4 h, while the water is continuously removed by means of a Dean-Stark apparatus. The mixture is cooled to ambient temperature. Diethyl ether (1 l) is added slowly and the mixture is cooled to 0° C., which results in precipitation of the product. The product is isolated by filtration, washed with ether (3×0.3 l) and dried under reduced pressure at 60° C., to give the compound (9) (303.20 g, 84%) in the form of a white crystalline product.

$^1$H NMR (300 MHz, DMSO-D$_6$): 2.28 (s, CH$_3$), 3.90 (s, CH$_2$), 5.25 (s, CH$_2$), 7.15 and 7.39 (AB, 4H), 7.37 (m, 5H).

b) Preparation of the Compound of Formula (8):

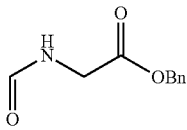

(8)

A 2.5 l Keller round-bottomed flask equipped with a reflux condenser, a thermometer, a dropping funnel and an argon conduit is loaded with methyl formate (700 ml), compound (9) (303.0 g, 898.0 mmol) and triethylamine (137 ml, 1 mol). The mixture is refluxed for 22 h. The conversion is followed by HPLC. The heterogeneous mixture is concentrated under reduced pressure, to give an oil (429 g). The product is dissolved in dichloromethane (1.5 l), washed with bicarbonate (2×0.5 l) and water (0.5 l). The combined aqueous phase is re-extracted with dichloromethane (0.5 l). The combined organic phase is dried (Na$_2$SO$_4$), filtered and concentrated under reduced pressure (40 mbar, 45° C., 1 h), to give the compound (8) (149.2 g, 86%) in the form of an orangey yellow oil.

$^1$H NMR (300 MHz, CDCl$_3$): 4.12 (d, CH$_2$), 5.19 (s, CH$_2$), 6.33 (broad singlet, NH), 8.23 (s, CHO).

c) Preparation of the Compound of Formula (7):

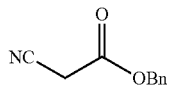

(7)

A 2.5 l Keller round-bottomed flask equipped with a reflux condenser, a thermometer, a dropping funnel and an argon conduit is loaded with the compound (8) (129.7 g, 671.3 mmol) and dichloromethane (1 l). The mixture is cooled to 0° C. Triethylamine (234 ml, 1678 mmol) is added to give a yellow solution. POCl₃ (102.9 g, 671.3 mmol) is added in 50 min, while the temperature is maintained at between 0 and 5° C. The mixture is stirred for a further 2 h while it is heated to ambient temperature. A solution of K₂CO₃ (134 g) in water (600 ml) is added slowly and carefully in small portions at between 25 and 30° C. After complete addition, the mixture is stirred for a further 1 h. Water (1 l) is added and the phases are separated. The organic phase is washed with water (0.2 l). The combined aqueous phase is re-extracted with dichloromethane (0.5 l). The combined organic phase is dried (Na₂SO₄), filtered and concentrated under reduced pressure, to give a brown oil (180 g). Chromatography is carried out on silica (500 g), elution being carried out with dichloromethane. The fractions containing the product are combined and concentrated under reduced pressure, to give an orangey-yellow oil. Storage at −10° C. allows crystallization of the compound (7) (101.9 g, 87%) so as to form a stable product.

¹H NMR (300 MHz, CDCl₃): 4, 22 (s, CH₂), 5.23 (s, CH₂), 7.38 (s, 5H).

Preparation 5

Preparation of the Compound of Formula (IX.1):

(IX.1)

A 4.5 l Keller round-bottomed flask equipped with a reflux condenser, a thermometer, a dropping funnel and an argon conduit is loaded with aluminum trichloride (297.00 g, 2.23 mol) and dichloromethane (2.3 l) and cooled to 0° C. A solution of trimethylsilylpropyne (250.00 g, 2.23 mol) and acetyl chloride (0.16 l, 2.23 mol) in dichloromethane (0.4 l) was added to the light yellow suspension in 1.5 h, the temperature being maintained at between 0 and 5° C. The brown solution with a certain amount of precipitated salt is heated to ambient temperature. The resulting reddish-brown solution is poured into ice/water (2 l). The layers are separated and the aqueous phase is extracted with dichloromethane (0.5 l). The combined organic phase is washed with water (0.5 l), dried (Na₂SO₄), filtered and concentrated under reduced pressure, to give a greenish-black liquid (558 g). The product is distilled at 180 mbar, to give a fraction (−160 g) that boils between 64 and 70° C. This product is again distilled at 210 mbar, to give the compound (IX.1) (90.30 g, 49%) in the form of a colorless liquid that has a boiling point of between 81 and 85° C.

¹H NMR (300 MHz, CDCl₃): 2.02 (s, CH₃), 2.31 (s, CH₃).

Preparation 6

Preparation of the Compound of Formula (VII.1):

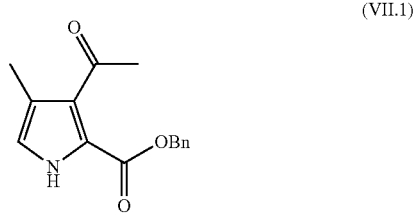 [SMILES: CC(=O)c1c(C)c[nH]c1C(=O)OCc1ccccc1]

(VII.1)

A 1 l Keller round-bottomed flask equipped with a reflux condenser, a thermometer, a dropping funnel and an argon conduit is loaded successively with the compound (7) (101.90 g, 0.58 mmol), dioxane (0.5 l) and the compound (IX.1) (52.53 g, 0.64 mol). When methyldiphenylphosphine (38.4 g, 0.19 mol) is added, the reaction becomes highly exothermic.

The reaction mixture becomes dark and is heated at 100° C. for 1 h. The conversion is followed by HPLC. The volatile products are removed under reduced pressure. The crude brown oil (209 g) is purified by chromatography on silica (2.1 kg), elution being carried out with a toluene/ethyl acetate (8/1) mixture. The fractions containing the pure product are combined and the volatile products are removed under reduced pressure, to give the compound (VII.1) (73.49 g, 49%) in the form of a light brown syrupy oil.

¹H NMR (300 MHz, CDCl₃): 2.13 (s, CH₃), 2.54 (s, CH₃), 5.32 (8s, CH₂), 6.68 (d, CH), 7.38 (m, 5H), 9.20 (broad singlet, NH).

RP-HPLC:

HP Hypersil BDS-C C18, 125×4 mm, 25° C.

Solvents with 0.1% of TFA: acetonitrile (ACN)-water: from 1 to 100% of ACN for 10 min, then 2 min with 100% of ACN Flow rate: 1 ml/min, detection at 220 nm Sample: 1 mg/1.5 ml of ACN Rt: 7.55 min (>91%)

Preparation 7

Preparation of the Pyrromethane of Formula (2):

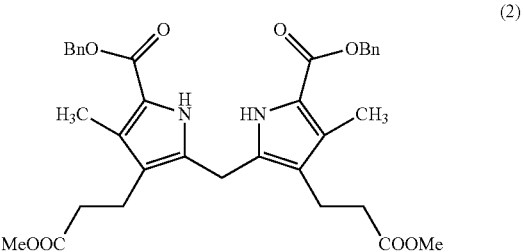 [SMILES: COC(=O)CCc1c(Cc2[nH]c(C(=O)OCc3ccccc3)c(C)c2CCC(=O)OC)[nH]c(C(=O)OCc2ccccc2)c1C]

(2)

A 4.5 l Keller round-bottomed flask equipped with a reflux condenser, a thermometer, a dropping funnel and an argon conduit is loaded with the compound (3) (52.0 g, 165.0 mmol) and diethyl ether (1.5 l). A freshly prepared solution of bromine (11.0 ml, 214.0 mmol) in diethyl ether (0.5 l) is added dropwise in 20 min at ambient temperature, so as to produce an orangey-brown solution. The conversion is followed by HPLC. If necessary, additional amounts of bromine are added. The mixture is again stirred at ambient temperature. The volatile products are removed under reduced pressure and the grayish-brown residue is dissolved in methanol (364 ml). The solution is heated at ~50° C. until complete conversion is obtained, (determined by HPLC after approximately 11 h). The dark reaction mixture is concentrated under reduced pressure until the product begins to crystallize. The precipitated product is isolated by filtration and washed with methanol (0.2 l). The crude product is recrystallized by suspending in diethyl ether (0.6 l) and refluxing, while heptane (1.8 l) is added and the heating is continued so as to maintain the mixture at reflux for a further 15 min. The mixture is cooled to ambient temperature and the product is isolated by filtration. The product is dried, to give the compound (2) (31.70 g, 63%) in the form of a light gray powder.

¹H NMR (300 MHz, CDCl₃): 2.21 (s, two CH₃), 2.43 (t, two CH₂), 2.68 (t, two CH₂), 3.50 (s, two CH₃), 3.89 (s, CH₂), 5.17 (s, two CH₂), 7.20 (m, 10H), 9.00 (broad singlet, two NH).

Preparation 8
Preparation of the Pyrromethane of Formula (I):

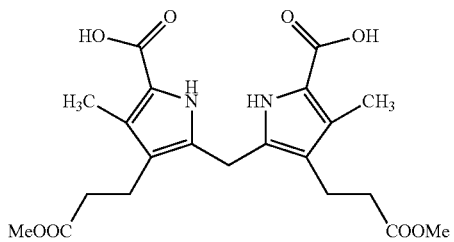
(1)

A low-pressure hydrogenation apparatus is loaded with the compound (2) (30.7 g, 49.9 mmol), THF (400 ml) and catalyst Pd/C at 10% (1.5 g, A027). The hydrogenation is carried out at ambient temperature under a hydrogen pressure atmosphere in 3 h. 2N ammonia 2N (0.1 l) is added to the reaction mixture and the catalyst is removed by filtration. The filtrate is adjusted to pH ~7 by adding acetic acid (60 ml). The solvent is removed under reduced pressure. The precipitated product is isolated by filtration, to give, after drying, the compound (I) (21.7 g, quantitative) in the form of a white powder.

$^1$H NMR (300 MHz, DMSO-D6): 2.18 (s, two $CH_3$), 2.20 (t, two $CH_2$), 2.59 (t, two $CH_2$), 3.60 (s, two $CH_3$), 3.82 (s, $CH_2$).

Preparation 9
Preparation of the Pyrromethane of Formula (II.1):

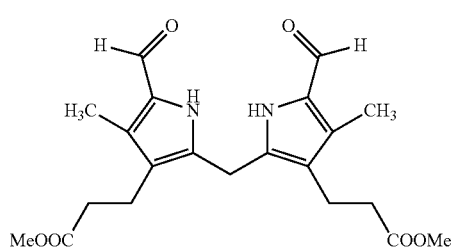
(II.1)

A 1 l Keller round-bottomed flask equipped with a reflux condenser, a thermometer, a dropping funnel and an argon conduit is loaded with trifluoroacetic acid (190 ml) and cooled to 0° C. The compound (I) (20.0 g, 46.0 mmol) is added in small portions in 10 min at 0° C. The mixture is stirred again at 0° C. for 1 h. The conversion is followed by HPLC. Trimethyl ortho-formate (57 ml) is added dropwise in 30 min, while the temperature is maintained at between 0 and 5° C. The reaction mixture is stirred for a further 1 h at 0° C. and then poured into water (1.7 l). The mixture is stirred vigorously for 10 min. The precipitated crude product is isolated by filtration and washed with water (0.3 l) in the form of an orange powder. The crude product is triturated in ethanol (0.2 l) and ammonia (0.4 l). The mixture is stirred for 30 min at ambient temperature and the product is isolated by filtration and washed with water (0.3 l) in the form of a dark yellow powder. The product is refluxed in methanol (0.4 l) for 10 min. The mixture is cooled to ambient temperature and the product is isolated by filtration and washed with cold methanol (0.1 l). The product is dried under reduced pressure, to give the compound (II.1) (15.30 g, 83%) in the form of a light yellow powder.

$^1$H NMR (300 MHz, $CDCl_3$): 2.30 (s, two $CH_3$), 2.53 (t, two $CH_2$), 2.81 (t, two $CH_2$), 3.72 (s, two $CH_3$), 4.06 (s, $CH_2$), 9.46 (s, two CHO), 10.43 (broad singlet, two NH).

RP-HPLC:
HP Hypersil BDS-C C18, 125×4 mm, 25° C.
Solvents with 0.1% of TFA: acetonitrile (ACN)-water: from 1 to 100% of ACN for 10 min, then 2 min with 100% of ACN
Flow rate: 1 ml/min, detection at 220 nm
Sample: 1 mg/1.5 ml of ACN
Rt: 6.78 min (>96%)

Preparation 10
Preparation of the Pyrromethane of Formula (V.1):

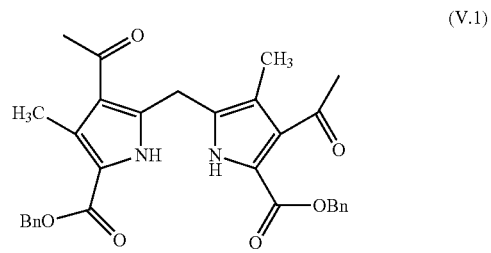 [SMILES: CC(=O)c1c(Cc2[nH]c(C(=O)OCc3ccccc3)c(C(C)=O)c2C)[nH]c(C(=O)OCc2ccccc2)c1C]
(V.1)

A 2.5 l Keller round-bottomed flask equipped with a reflux condenser, a thermometer, a dropping funnel and an argon conduit is loaded with the compound (VII.1) (50.0 g, 194.4 mmol), the compound (VI.1) (51.3 g, 155.6 mmol) and dichloroethane (1.1 l). The mixture is heated to 40° C., to give an orangey-red solution. $HBF_4$ etherate (2.35 ml (54%), 9.3 mmol) is added and the mixture is heated rapidly to 90° C. The conversion is followed by HPLC. After 1 h, the mixture is cooled rapidly to ambient temperature and poured into a saturated bicarbonate solution (0.5 l). The layers are separated and the aqueous phase is extracted with dichloroethane (0.5 l). The combined organic extracts are dried ($Na_2SO_4$), filtered, stirred with Norrit C (2 g), filtered and completely concentrated under reduced pressure, to give a sticky brown syrup (96.5 g). The crude product is dissolved in methanol (0.3 l), concentrated under reduced pressure and again dissolved in methanol (150 ml). Germination crystals are added and the mixture is left to stand for 15 h at ambient temperature while the product crystallizes. The supernatant is removed and the crystals (fraction K1, 34.3 g) are washed with methanol. The combined methanol fractions are completely concentrated under reduced pressure and chromatographed on silica (420 g), elution being carried out with hexane/ethyl acetate (2/1). The fractions containing the product are combined and concentrated under reduced pressure. The product is recrystallized as above in methanol, to give a fraction K2 (16.7 g). The supernatant is again chromatographed on silica (400 g), elution being carried out with hexane/ethyl acetate (2/1). The fractions containing the product are combined and concentrated under reduced pressure. The product is recrystallized as above from methanol, to give a fraction K3 (3.7 g). The product fractions (K1-K3) are combined, dissolved in toluene and completely concentrated under reduced pressure. After drying under reduced pressure at 50° C. for 1 h, the compound (V.1) (54.7 g, 68%) is recovered in the form of off-white crystals.

$^1$H NMR (300 MHz, $CDCl_3$): 2.09 (2.09, $CH_3$), 2.49 (s, $CH_3$), 2.50 (s, $CH_3$), 2.58 (s, $CH_3$), 4.04 (s, $CH_2$), 5.27 (s, $CH_2$), 5.29 (s, $CH_2$), 7.35 (m, 10H), 10.5 (broad singlet, NH).

Preparation 11
Preparation of the Pyrromethane of Formula (IV.1):

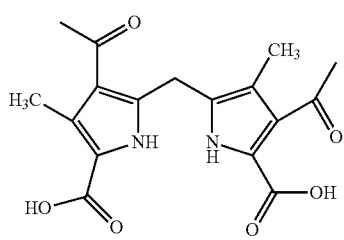

(IV.1)

A low-pressure hydrogenation apparatus is loaded with the compound (V.1) (54.3 g, 103.1 mmol), tetrahydrofuran (700 ml), triethylamine (20.8 g, 206.2 mmol) and catalyst Pd/C at 10% (2.75 g). The hydrogenation is carried out at ambient temperature under a hydrogen pressure atmosphere in 3 h. The catalyst is removed by filtration. The filtrate is concentrated under reduced pressure. After drying under reduced pressure at 45° C. for 0.5 h, the compound (IV.1) (54.7 g, quantitative) is recovered in the form of an off-white foam, in the form of a monotriethylamine salt containing residual amounts of toluene and of THF.

$^1$H NMR (300 MHz, DMSO-D6): 1.97 (s, CH$_3$), 2.38 (s, CH$_3$), 2.52 (s, two CH$_3$), 4.14 (s, CH$_2$).

Preparation 12
Preparation of the Pyrromethane of Formula (IIIa):

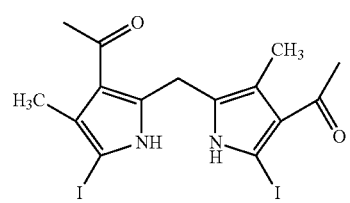

(IIIa)

A 2.5 l Keller round-bottomed flask equipped with a reflux condenser, a thermometer, a dropping funnel and an argon conduit is loaded with solid NaHCO$_3$ (55.6 g, 662.0 mmol), water (900 ml) and ethanol (300 ml). A solution of the compound (IV.1) (54.3 g, 101.9 mmol) in ethanol (300 ml) is added. A solution of iodine (64.7 g, 254.9 mmol) in ethanol (400 ml) is added, at ambient temperature, to give a brown heterogeneous mixture. A certain amount of foaming and a reduced exothermia are observed. The conversion is followed by HPLC. The reaction mixture is stirred again at ambient temperature for 5 h. The reaction mixture is diluted with water (0.1 l) and the precipitated product is isolated by filtration. The precipitate is washed with water (3×0.1 l), ethanol (2×0.1 l) and ether (2×0.1 l). After drying of the crystals of product under reduced pressure at 60° C., the compound (III.a) (48.1 g, 92%) is recovered in the form of light red crystals.

$^1$H NMR (300 MHz, DMSO-D$_6$): 2.06 (s, CH$_3$), 2.15 (s, CH$_3$), 2.33 (s, CH$_3$), 4.08 (s, CH$_2$).

RP-HPLC:

HP Hypersil BDS-C C18, 125×4 mm, 25° C.

Solvents with 0.1% of TFA: acetonitrile (ACN)-water: from 1 to 100% of ACN for 10 min, then 2 min with 100% of ACN Flow rate: 1 ml/min, detection at 220 nm Sample: 1 mg/1.5 ml of ACN Rt: 8.13 min (>92%)

Preparation 13
Preparation of the Porphyrin of Formula (Ia.1):

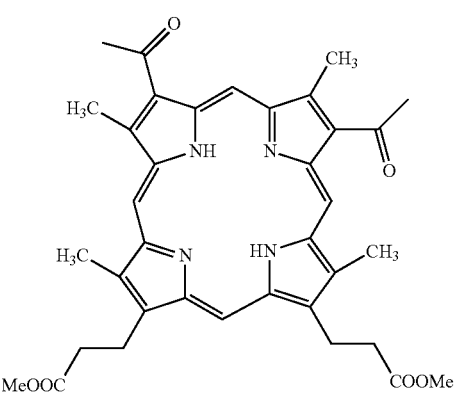

(Ia.1)

A 2.5 l Keller round-bottomed flask equipped with a reflux condenser, a thermometer, a dropping funnel and an argon conduit is loaded with acetic acid anhydride (290 ml), acetic acid (1.8 l) and trifluoromethanesulfonic acid (4.95 ml, 56.77 mmol). A substantially homogeneous solution of the compound (II.1) (12.00 g, 29.82 mmol) and of the compound (IIIa) (14.48 g, 28.40 mmol) in acetic acid (400 ml) is added, at ambient temperature, in 5 min, which produces a blood red solution. No exothermia is observed. The mixture is stirred again at ambient temperature for 1 h, with the formation of a certain precipitate. The conversion is followed by HPLC. A solution of NaOAc (9.4 g) in acetic acid (100 ml) is added, to give a dark brown solution. After 10 min, the volatile products are removed under reduced pressure and dried under reduced pressure for 1.5 h at 50° C. The dark residue is taken up in dichloromethane (300 ml), and water (500 ml) without vigorous mixing. The organic layer is separated and the aqueous phase is extracted with dichloromethane (0.3 l). The combined organic phase is dried (Na$_2$SO$_4$), filtered and concentrated, to give a black crystalline product (31.3 g). The mixture is dissolved in dichloromethane and applied to a column of silica gel (1 kg) covered with dichloromethane/acetone (95/5). The product is eluted with a gradient of 95/5 to 90/10. The fractions contained in the product are combined and completely concentrated under reduced pressure. The compound (Ia.1) (9.97 g, 55%) is recovered in the form of violet-black crystals.

$^1$H NMR (300 MHz, CDCl$_3$): 3.15 (two t, two CH$_2$), 3.17 (s, CH$_3$), 3.25 (s, CH$_3$), 3.39 (s, CH$_3$), 3.50 (s, CH$_3$), 3.60 (s, CH$_3$), 3.64 (s, CH$_3$), 3.65 (s, CH$_3$), 3.71 (s, CH$_3$), 4.22 (two t, two CH$_2$), 9.50 (s, CH), 9.59 (s, CH), 10.43 (s, CH), 10.46 (s, CH).

RP-HPLC:

HP Hypersil BDS-C C18, 125×4 mm, 25° C.

Solvents with 0.1% of TFA: acetonitrile (ACN)-water: from 1 to 100% of ACN for 10 min, then 3 min with 100% of ACN Flow rate: 1 ml/min, detection at 220 nm Sample: 1 mg/1.5 ml of ACN Rt: 11.66 min (>93%)

Preparation 14
Preparation of the Porphyrin of Formula (Ib.1):

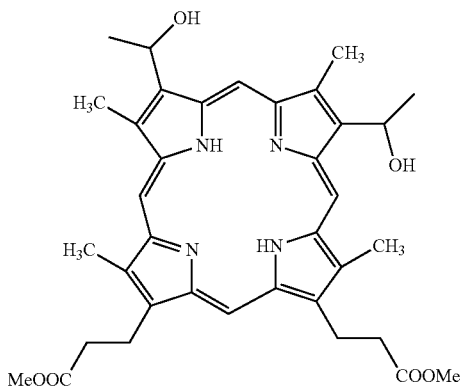
(Ib.1)

A 1 l Keller round-bottomed flask equipped with a reflux condenser, a thermometer, a dropping funnel and an argon conduit is loaded with the compound (Ia.1) (9.86 g, 15.84 mmol), dichloromethane (500 ml) and methanol (24 ml). $NaBH_4$ (3.00 g, 79.32 mmol) is added portionwise to the reddish-brown mixture. A certain foaming is observed. The reaction is closely followed by HPLC. After 80 min, the mixture is poured into a mixture of water (500 ml) and 4N HCl (80 ml). Gas is seen to be given off. The mixture is neutralized by adding solid $NaHCO_3$. The layers are separated and the aqueous phase is extracted with dichloromethane (2×300 ml). The combined organic extracts are dried ($Na_2SO_4$), filtered and concentrated under reduced pressure. After drying under reduced pressure at 50° C. for 0.5 h, the compound (Ib.1) in the form of a mixture of two stereoisomers (9.58 g, 96%) is recovered in the form of violet-black crystals.

$^1$H NMR (300 MHz, $CDCl_3$): 1.92 (m, 6H, two $CH_3$), 3.16 (m, 4H, two $CH_2$), 3.28, 3.30, 3.33 and 3.35 (4s, 6H, two $CH_3$), 3.43 (s, 6H, two $CH_3$), 3.66 (s, 6H, two $CH_3$), 4.20 (m, 4H, two $CH_2$), 6.05 (m, 2H, two CH), 9.73, 9.74, 9.75, 9.76, 10.00, 10.02, 10.08 and 10.10 (8s, total 4H, four CH).

RP-HPLC:
HP Hypersil BDS-C C18, 125×4 mm, 25° C.
Solvents with 0.1% of TFA: acetonitrile (ACN)-water: from 1 to 100% of ACN for 10 min, then 3 min with 100% of ACN
Flow rate: 1 ml/min, detection at 220 nm
Sample: 1 mg/1.5 ml of ACN
Rt: 7.90 min, 51% and 8.01 min, 49%

Preparation 15
Preparation of the Porphyrin of Formula (Ic.1):

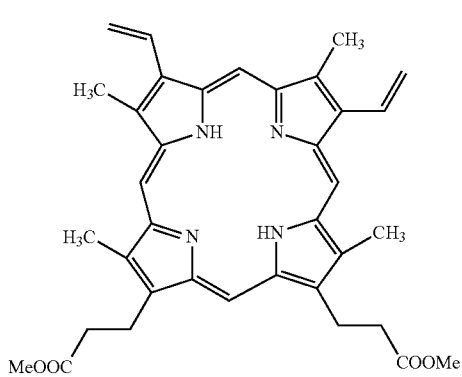
(Ic.1)

A 1 l Keller round-bottomed flask equipped with a reflux condenser, a thermometer, a dropping funnel and an argon conduit is loaded with the compound (Ib.1) (9.48 g, 15.12 mmol) and DMF (400 ml) and the mixture is degassed with argon. Benzoyl chloride (45.0 ml, 387.9 mmol) is added and the mixture is rapidly heated to 100° C. The mixture is stirred again at 100° C. for 1 h. The conversion is followed by HPLC. The reaction mixture is cooled rapidly and the volatile products are removed under reduced pressure. The residue is dissolved in dichloromethane (0.3 l) and stirred vigorously with a water/methanol (0.3 l) mixture. The layers are separated and the aqueous phase is extracted with dichloromethane (2×0.2 l). The combined organic extracts are washed with bicarbonate (0.3 l), dried ($Na_2SO_4$) and filtered. The filtrate is treated with silica (20 g) and filtered. Methanol (50 ml) is added and the mixture is then concentrated under reduced pressure, while crystallization takes place toward the end, to give a violet-black product (20 g). The product is triturated with methanol at 50° C. for 0.5 h. After cooling to ambient temperature, chloroform (2 ml) is added and the product is isolated by filtration. After drying under reduced pressure at 50° C. for 15 h, the compound (Ic.1) (6.34 g, 77%) is recovered in the form of shiny violet-black crystals.

$^1$H NMR (300 MHz, $CDCl_3$): 3.23 (t, two $CH_3$), 3.52 (s, $CH_3$), 3.54 (s, $CH_3$), 3.58 (s, $CH_3$), 3.64 (s, $CH_3$), 3.64 (s, $CH_3$), 3.65 (s, $CH_3$), 3.66 (s, $CH_3$), 4.32 (t, two $CH_2$), 6.11-6.34 (m, 4H, two $CH_2$=), 8.10-8.23 (m, 2H, two CH=), 9.85, 9.86, 9.97 and 9.98 (4s, 4CH).

RP-HPLC:
HP Hypersil BDS-C C18, 125×4 mm, 25° C.
Solvents with 0.1% of TFA: acetonitrile (ACN)-water: from 1 to 100% of ACN for 10 min, then 6 min with 100% of ACN
Flow rate: 1 ml/min, detection at 220 nm
Sample: 1 mg/1.5 ml of ACN
Rt: 12.43 min (>97%)

Preparation 16
Preparation of the porphyrin of formula (IC.2, 2Na):

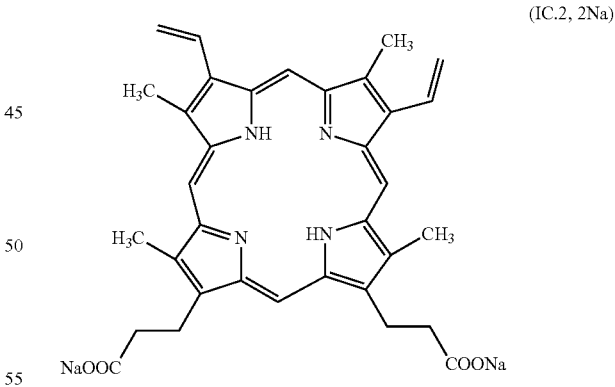
(IC.2, 2Na)

A 2.5 l Keller round-bottomed flask equipped with a reflux condenser, a thermometer, a dropping funnel and an argon conduit is loaded with the compound (Ic.1) (6.30 g, 10.67 mmol) and dichloromethane (200 ml). The product is dissolved by heating to 40° C. At 40° C., methanol (400 ml) followed by 4N NaOH (200 ml) are successively added. The formation of a precipitate is observed. The mixture is refluxed. The conversion is followed by HPLC. The organic volatile products are removed under reduced pressure. The suspension is filtered through a glass fiber filter. The product is washed with water (3×0.1 l), methanol (3×30 ml) and diethyl ether (2×30 ml). After drying under reduced pressure at 70° C. for 2 h, then at 40° C. for 15 h, the compound (Ic.2, 2Na) (6.06 g, 94%) is recovered in the form of a violet-black solid product.

$^1$H NMR (300 MHz, TFA-D$_1$): 3.45 (two t, two CH$_2$), 3.82 (s, CH$_3$), 3.85 (s, CH$_3$), 3.88 (s, CH$_3$), 3.91 (s, CH$_3$), 4.73 (two t, two CH$_2$), 6.43-6.70 (m, 4H, two CH$_2$=), 8.28-8.40 (m, 2H, two CH=), 11.08, 11.11, 11.15, and 11.27 (4s, 4CH).

RP-HPLC:

HP Hypersil BDS-C C18, 125×4 mm, 25° C.

Solvents: acetonitrile (ACN) with 0.1% of TFA-water with 0.1% of TFA: from 1 to 100% of ACN for 10 min, then 6 min with 100% of ACN Flow rate: 1 ml/min, detection at 220 nm Sample: 0.1 mg/1.5 ml of AcOH/DMF Rt: 9.85 min (>98%)

| Elemental analysis | | |
|---|---|---|
| Theory for C34•H32•N4.04•Na$_2$ (MW 606.63) | | Result |
| C | 67.32 +/− 0.3% m/m | 64.91% m/m |
| H | 5.32 +/− 0.3% m/m | 5.38% m/m |
| N | 9.24 +/− 0.3% m/m | 8.94% m/m |
| Water | | 3.56% m/m |
| Na | 7.58 m/m | 7.15% m/m |

With measurements adjusted after the addition of 1.24 mol of water (amount of water measured by Karl-Fisher titration) per mole of product.

| Theory for C34•H32•N4.04•Na2•1.24 H$_2$O (MW 636.54) | | Result |
|---|---|---|
| C | 64.93 +/− 0.3% m/m | 64.91% m/m |
| H | 5.28 +/− 0.3% m/m | 5.38% m/m |
| N | 8.91 +/− 0.3% m/m | 8.94% m/m |
| Water | 3.56 m/m | 3.56% m/m |
| Na | 7.31 m/m | 7.15% m/m |

What is claimed is:

1. A process for preparing a metal complex of compound of formula (I″), optionally in the form of a salt:

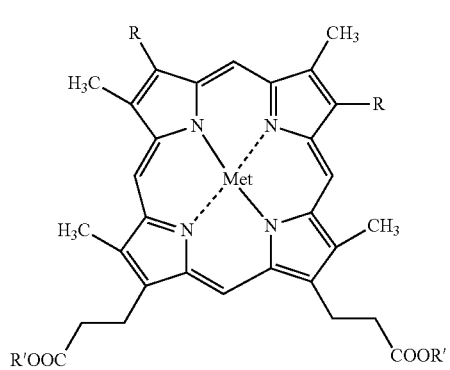

in which:

R is hydrogen, —CH=CH$_2$, —CH$_2$—CH$_3$, —CH(OH)CH$_3$, —C(O)CH$_3$ or —CH$_2$CH$_2$COOR′a, with R′a being hydrogen, methyl, ethyl, n-propyl or i-propyl, R′ is hydrogen, or R′b, wherein R′b is methyl, ethyl, n-propyl or i-propyl, the method comprising complexing the metal, the salt of the metal or the hydroxide of metal with the product of the condensation of a compound of formula (II):

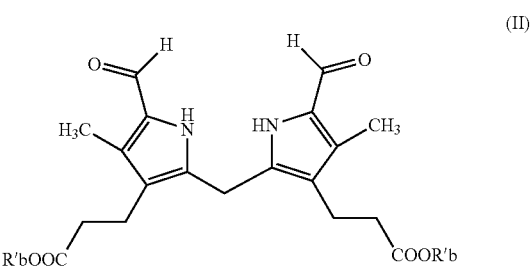

in which R′b is as defined above for (I″), with a compound of formula (III):

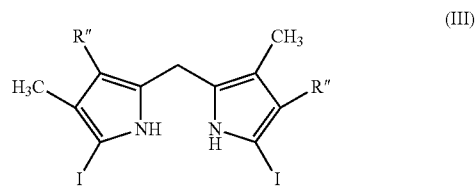

in which R″ is selected from hydrogen, —CH=CH$_2$, —CH$_2$—CH$_3$, —C(O)CH$_3$, —CH(OH)CH$_3$, —CH$_2$CH$_2$OH, —CH$_2$CH$_2$OC(O)CH$_3$, —CH$_2$CH$_2$Cl, and —CH$_2$CH$_2$COOR′a, wherein R′a is hydrogen, methyl, ethyl, n-propyl, or i-propyl so as to form the compound of formula (I′):

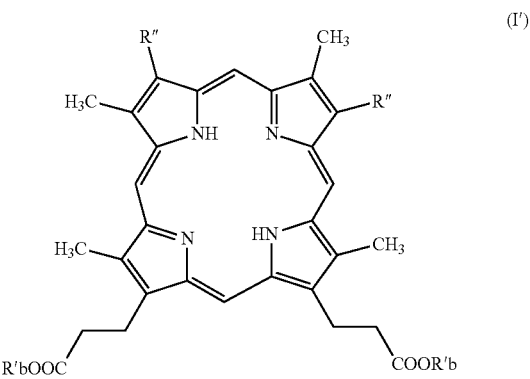

in which R" and R'b are as defined above for (II) and (III), and, when R" and R are not the same moiety, further comprising converting R" to R, and when R'=H, further comprising eliminating R'b so as to form —COOH moieties, optionally in the form of a salt.

2. The process as claimed in claim 1,
wherein Met is selected from a divalent metal M(II) and a metal salt of a trivalent metal M(III)X, X is selcted from Cl and OH and M is selected from iron, gallium, nickel, zinc, palladium, cobalt, calcium and magnesium.

3. The process as claimed in claim 2, wherein the final product is heme, hemin or hematin.

4. The method of claim 1 wherein in the compound of formula (I") R is a —CH=CH$_2$ group, and wherein the process for forming said condensation product used in the metal complex comprises condensing, in an acidic medium, a compound of formula (II):

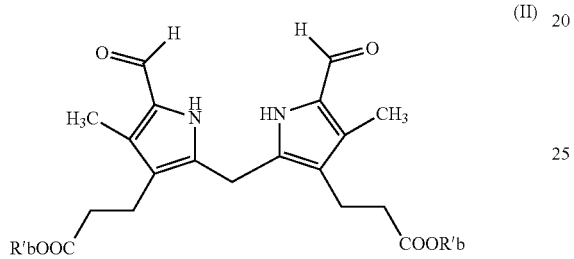

in which R'b is as defined above for (I"),
with a compound of formula (III):

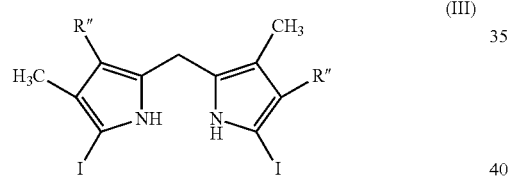

in which R" is —CH$_2$CH$_2$OH, —CH$_2$CH$_2$Cl, —CH$_2$CH$_2$OC(O)CH$_3$, —CH(OH)CH$_3$ or —C(O)CH$_3$, followed by conversion of the groups R" to R, and when R'=H, further comprising eliminating the groups R'b so as to form —COOH moieties, optionally in the form of a salt.

5. The method of claim 4 wherein the compound of formula (I') is a compound of formula (IC):

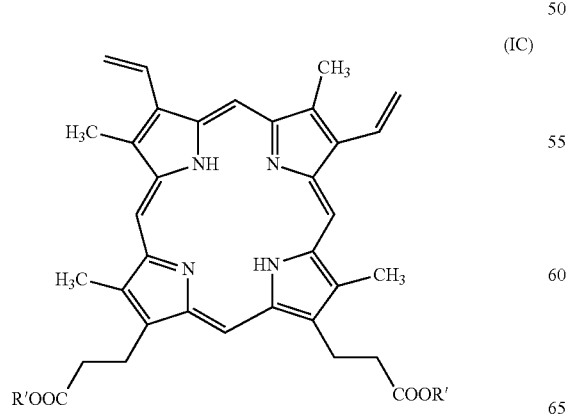

in which R' is as defined for (I"), or a salt thereof, by coupling a compound of formula (II):

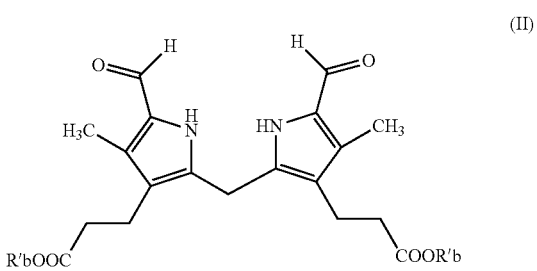

in which R'b is as defined above for (I"),
with a compound of formula (IIIa):

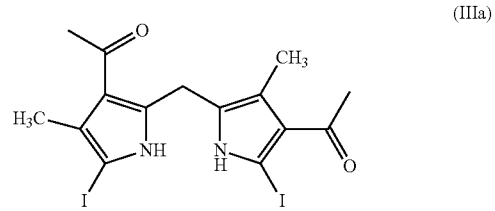 [SMILES: CC(=O)c1c(I)[nH]c(Cc2[nH]c(I)c(C)c2C(C)=O)c1C]

so as to form the compound of formula (Ia):

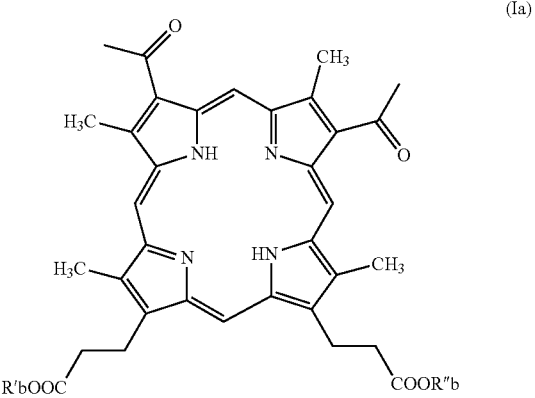

in which R'b is as defined for (I"),
followed:
by reducing the —C(O)CH$_3$ moieties, resulting in the formation of the compound of formula (Ib):

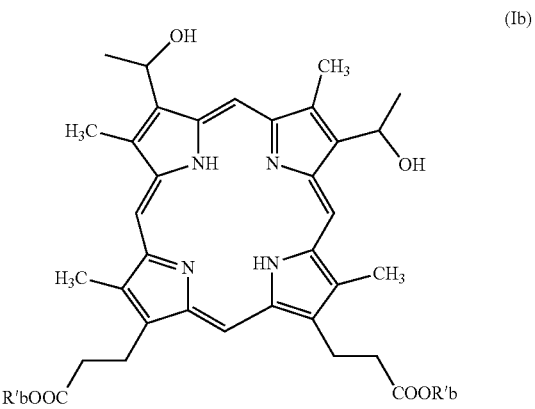

in which R'b is as defined for (I"), followed by converting the —CH(OH)CH₃ groups to —CH=CH₂ groups, and, when R' is a hydrogen atom, eliminating R'b moieties by hydrolysis, or, when the compound (IC) to be formed is in the form of a salt, further comprising eliminating R'b moieties by saponification.

6. The process as claimed in claim 5, wherein the reaction that converts the —CH(OH)CH₃ groups to the —CH=CH₂ groups is carried out in the presence of an acid halide.

7. The process as claimed in claim 6, wherein the reaction that converts the —CH(OH)CH₃ groups to —CH=CH₂ groups is carried out in an aprotic polar solvent.

8. The process as claimed in one of claims 5 to 7, wherein the reduction of the —C(O)CH₃ moieties is carried out in the presence of a hydride.

9. The process as claimed in claim 8, wherein the reduction of the —C(O)CH₃ moieties is carried out in dichloromethane in the presence of methanol.

10. The process as claimed in claim 9, wherein R'b is a methyl group.

11. The process as claimed in claim 9 wherein the compound of formula (I') is protoporphyrin (IX) in the form of the sodium salt of formula (IC.2, 2Na):

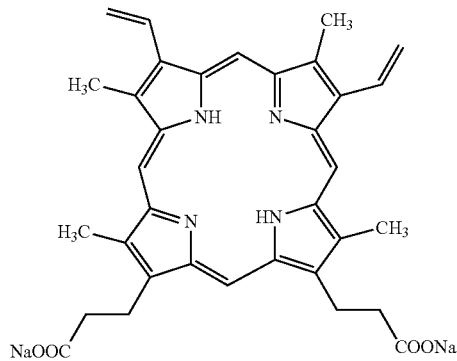

(IC.2, 2Na)

further comprising saponifying the compound of formula (Ic):

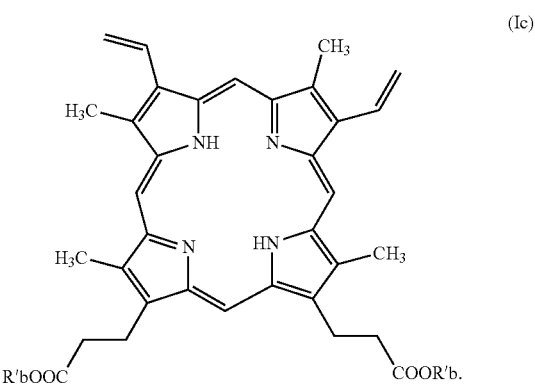

(Ic)

12. The process as claimed in claim 11, wherein the saponification is carried out in dichloromethane at reflux.

13. The process of claim 1 wherein Met is iron, and the formation of the metal complex is carried out by treatment with FeSO₄ followed by treatment with sodium hydroxide.

14. The process of claim 1 wherein Met is iron and the formation of the metal complex is carried out by the action of FeCl₂, in a dichloromethane/acetonitrile mixture under an inert atmosphere.

* * * * *